(12) United States Patent
Bakajin et al.

(10) Patent No.: US 8,940,173 B2
(45) Date of Patent: *Jan. 27, 2015

(54) MEMBRANES WITH FUNCTIONALIZED CARBON NANOTUBE PORES FOR SELECTIVE TRANSPORT

(75) Inventors: Olgica Bakajin, San Leandro, CA (US); Aleksandr Noy, Belmont, CA (US); Francesco Fornasiero, Oakland, CA (US); Hyung Gyu Park, Zurich (CH); Jason K. Holt, San Francisco, CA (US); Sangil Kim, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 547 days.

This patent is subject to a terminal disclaimer.

(21) Appl. No.: 12/995,160

(22) PCT Filed: May 29, 2009

(86) PCT No.: PCT/US2009/045675
§ 371 (c)(1),
(2), (4) Date: Jun. 2, 2011

(87) PCT Pub. No.: WO2009/148959
PCT Pub. Date: Dec. 10, 2009

(65) Prior Publication Data
US 2011/0220574 A1    Sep. 15, 2011

Related U.S. Application Data

(60) Provisional application No. 61/056,940, filed on May 29, 2008.

(51) Int. Cl.
*B01D 11/00* (2006.01)
*B01D 61/00* (2006.01)
(Continued)

(52) U.S. Cl.
CPC ............... *C02F 1/44* (2013.01); *B01D 53/228* (2013.01); *B01D 61/025* (2013.01);
(Continued)

(58) Field of Classification Search
CPC .......... B82Y 30/00; B82Y 40/00; B82Y 5/00; B82Y 10/00; B82Y 20/00; B82Y 99/00; B82Y 15/00; B01D 61/025; B01D 61/027; B01D 67/0079; B01D 69/148; B01D 71/021; B01D 71/16; B01D 2325/02; B01D 69/043
USPC ............... 210/500.27, 500.25, 502.1, 500.38, 210/652, 645; 264/41, 555; 977/751; 423/304.4, 447.23; 427/291; 428/304.4
See application file for complete search history.

(56) References Cited

U.S. PATENT DOCUMENTS 4,302,336 A   11/1981   Kawaguchi et al.
4,434,057 A   2/1984    Marquardt
(Continued)

FOREIGN PATENT DOCUMENTS

EP    1 340 544 A1    9/2003
GB    2 399 092 A     9/2004
(Continued)

OTHER PUBLICATIONS

Scott A. Miller et al; Electoosmotic Flow in Template-prepared Carbon Nanotube Membranes; J. Am. Chem. Soc. 2004, 123, 12335-12342.*
(Continued)

*Primary Examiner* — Ana Fortuna
(74) *Attorney, Agent, or Firm* — Foley & Lardner LLP

(57) ABSTRACT

Provided herein composition and methods for nanoporous membranes comprising single walled, double walled, or multi-walled carbon nanotubes embedded in a matrix material. Average pore size of the carbon nanotube can be 6 nm or less. These membranes are a robust platform for the study of confined molecular transport, with applications in liquid and gas separations and chemical sensing including desalination, dialysis, and fabric formation.

29 Claims, 18 Drawing Sheets

(51) Int. Cl.

| | | |
|---|---|---|
| *B01D 39/00* | (2006.01) | |
| *B01D 39/14* | (2006.01) | |
| *B01D 71/06* | (2006.01) | |
| *C02F 1/44* | (2006.01) | |
| *B01D 53/22* | (2006.01) | |
| *B01D 61/02* | (2006.01) | |
| *B01D 67/00* | (2006.01) | |
| *B01D 69/14* | (2006.01) | |
| *B01D 71/02* | (2006.01) | |
| *B82Y 30/00* | (2011.01) | |
| *A61M 1/34* | (2006.01) | |
| *C02F 103/08* | (2006.01) | |

(52) U.S. Cl.
CPC ......... *B01D 61/027* (2013.01); *B01D 67/0072* (2013.01); *B01D 67/0079* (2013.01); *B01D 69/148* (2013.01); *B01D 71/02* (2013.01); *B01D 71/021* (2013.01); *B01D 71/024* (2013.01); *B01D 71/027* (2013.01); *B82Y 30/00* (2013.01); *A61M 1/34* (2013.01); *B01D 2256/10* (2013.01); *B01D 2256/22* (2013.01); *B01D 2256/24* (2013.01); *B01D 2257/102* (2013.01); *B01D 2257/504* (2013.01); *B01D 2323/36* (2013.01); *B01D 2325/18* (2013.01); *C02F 1/442* (2013.01); *C02F 2103/08* (2013.01); *C02F 2305/08* (2013.01); *Y02C 10/10* (2013.01)
USPC ... 210/645; 210/652; 210/502.1; 210/500.27; 210/500.25

(56) References Cited

U.S. PATENT DOCUMENTS

| | | | |
|---|---|---|---|
| 4,611,053 A | 9/1986 | Sasa | |
| 5,051,178 A | 9/1991 | Uemura et al. | |
| 5,102,550 A | 4/1992 | Pizzino et al. | |
| 5,376,253 A | 12/1994 | Rychen et al. | |
| 5,698,175 A | 12/1997 | Hiura et al. | |
| 6,337,018 B1 | 1/2002 | Mickols | |
| 6,824,689 B2 | 11/2004 | Wang et al. | |
| 6,858,197 B1 | 2/2005 | Delzeit | |
| 6,863,942 B2 | 3/2005 | Ren et al. | |
| 7,205,069 B2 * | 4/2007 | Smalley et al. | 429/129 |
| 7,211,320 B1 * | 5/2007 | Cooper et al. | 428/306.6 |
| 7,229,556 B1 * | 6/2007 | Hinds et al. | 210/652 |
| 7,290,667 B1 * | 11/2007 | Bakajin et al. | 210/503 |
| 7,301,191 B1 | 11/2007 | Tombler et al. | |
| 7,413,723 B2 | 8/2008 | Niu et al. | |
| 7,419,601 B2 * | 9/2008 | Cooper et al. | 210/679 |
| 7,439,731 B2 | 10/2008 | Crafts et al. | |
| 7,459,121 B2 | 12/2008 | Liang et al. | |
| 7,473,411 B2 | 1/2009 | Ajayan et al. | |
| 7,611,628 B1 | 11/2009 | Hinds | |
| 7,623,340 B1 | 11/2009 | Song et al. | |
| 7,931,838 B2 * | 4/2011 | Marand et al. | 264/101 |
| 7,993,524 B2 | 8/2011 | Ratto et al. | |
| 8,029,856 B2 | 10/2011 | Miyoshi et al. | |
| 8,038,887 B2 * | 10/2011 | Bakajin et al. | 210/652 |
| 8,177,979 B2 | 5/2012 | Ratto et al. | |
| 8,196,756 B2 | 6/2012 | Ratto et al. | |
| 8,286,803 B2 | 10/2012 | Nowak et al. | |
| 2003/0116503 A1 | 6/2003 | Wang et al. | |
| 2003/0121857 A1 | 7/2003 | Kurth et al. | |
| 2003/0165418 A1 | 9/2003 | Ajayan et al. | |
| 2004/0173506 A1 | 9/2004 | Doktycz et al. | |
| 2005/0079379 A1 | 4/2005 | Wadsworth et al. | |
| 2006/0073089 A1 | 4/2006 | Ajayan et al. | |
| 2007/0137701 A1 | 6/2007 | Sainte Catherine et al. | |
| 2008/0149561 A1 | 6/2008 | Chu et al. | |
| 2008/0290020 A1 * | 11/2008 | Marand et al. | 210/500.27 |
| 2009/0321355 A1 * | 12/2009 | Ratto et al. | 210/651 |
| 2010/0025330 A1 * | 2/2010 | Ratto et al. | 210/651 |
| 2010/0206811 A1 * | 8/2010 | Ng et al. | 210/654 |
| 2011/0253630 A1 | 10/2011 | Bakajin et al. | |
| 2012/0080378 A1 | 4/2012 | Revanur et al. | |
| 2012/0080380 A1 * | 4/2012 | Wang et al. | 210/654 |
| 2012/0241371 A1 | 9/2012 | Revanur et al. | |
| 2012/0285890 A1 * | 11/2012 | Koehler et al. | 210/651 |

FOREIGN PATENT DOCUMENTS

| | | |
|---|---|---|
| WO | WO 2005/001021 A | 1/2005 |
| WO | WO 2007/025104 * | 1/2007 |

OTHER PUBLICATIONS

Acharya, M. et al.(2000) "Transport in Nanoporous Carbon Membranes: Experiments and Analysis," AlChe J. 46(5):911-922.

Ackerman, D.M. et al. (2003) "Diffusivities of Ar and Ne in Carbon Nanotubes," Molecular Simulation 29(10-11):677-684.

Agre, P. et al. (2001) "Discovery of the Aquaporins and Their Impact on Basic and Clinical Physiology," Curr. Top. Membr. 51:1-38.

Bass, R.B. et al. (2002) "Crystal Structure of *Escherichia coli* MscS, a Voltage-Modulated and Mechanosensitive Channel," Science 298:1582-1587.

Baudry, J. et al. (2001) "Experimental Evidence for a Large Slip Effect at a Nonwetting Fluid-Solid Interface," Langmuir 17:5232-5236.

Beckstein, O. et al. (2004) "Not Ions Alone: Barriers to Ion Permeation in Nanopores and Channels," J Am Chem Soc. 126(45):14694-14695.

Beckstein, O. et al. (2004) "The influence of geometry, surface character and flexibility on thepermeation of ions and water through biological pores" Phys. Biol. 1:42-52.

Berezhkovskii, A. et al. (2002) "Single-File Transport of Water Molecules through a Carbon Nanotube," Physical Review Letters 89(6):064503-1-064503-4.

Bhatia, S.K. et al. (2005) "Comparisons of diffusive and viscous contributions to transport coefficients of light gases in single-walled carbon nanotubes," Molecular Simulation 31(9):643-649.

Bird et al. (1960) "§ 1.4 Theory of Viscosity of Gases at Low Density," Transport Phenomena Wiley, Ed. (New York), pp. 19-26.

Bittner, E.W. et al. (2003) "Characterization of the surfaces of single-walled carbon nanotubes using alcohols and hydrocarbons: a pulse adsorption technique," Carbon 41:1231-1239.

Cervera, J. et al. (2001) "Ion size effects on the current efficiency of narrow charged pores," J. Membrane Sci. 191:179-187.

Chen, H. et al.(2006) "Predictions of selectivity and flux for $CH_4/H_2$ separations using single walled carbon nanotubes as membranes," J. Memb. Sci. 269:152-160.

Chen, H. et al. (2006) "Transport Diffusion of Gases is Rapid in Flexible Carbon Nanotubes," J. of Phys. Chem. B 110:1971-1975.

Carter, D.J. et al. (2003) "Incorporation of Cyano Transition Metal Complexes in KCl Crystals—Experimental and Computational Studies," Aust. J. Chem. 56:675-678.

Childress, A.E. et al. (2000) "Relating Nanofiltration Membrane Performance to Membrane Charge (Electrokinetic) Characteristics," Environ. Sci. Technol. 34(17):3710-3716.

Chopra, N. et al. (2005) "Bifunctional carbon nanotubes by side wall protection," Adv. Funct. Mater. 15(5):858-864.

Cooper, S.M. et al. (2004) "Gas Transport Characteristics through a Carbon Nanotube," Nano Lett. 4(2):377-381.

Cottin-Bizonne, C. et al. (2002) "Nanorheology: An investigation of the boundary condition at hydrophobic and hydrophilic interfaces," Eur. Phys. J. E 9:47-53.

Craig, V.S.J. et al. (2001) "Shear-Dependent Boundary Slip in an Aqueous Newtonian Liquid," Phys. Rev. Let. 87(5):054504-1-054504-4.

Cui, H. et al. (2000) "Deposition of aligned bamboo-like carbon nanotubes via microwave plasma enhanced chemical vapor deposition," J. Appl. Phys. 88(10):6072-6074.

de Lint, W.B. et al. (2004) "Predictive charge-regulation transport model for nanofiltration from the theory of irreversible processes," J. Membrane Sci. 243: 365-377.

(56) References Cited

OTHER PUBLICATIONS

Dechadilok, P. et al. (2006) "Hindrance factors for diffusion and convection in pores," Ind. Eng. Chem. Res. 45:6953-6959.
Deen, W.M. (1987) "Hindered transport of large molecules in liquid-filled pores," AIChE 33(9):1409-1425.
Donnan, F.G. (1924) "The theory of membrane equilibria," Chem Rev 1:73-90.
Donnan, F.G. (1995) "Theory of membrane equilibria and membrane potentials in the presence of non-dialysing electrolytes—A contribution to physical-chemical physiology," Journal of Membrane Science 100(1):45-55. (Reprinted from Zeitshrift fur Electrochemie and Angewandte Physikalische Chemie (1911) 17: 572).
Doyle, D.A. et al. (1998) "The Structure of the Potassium Channel: Molecular Basis of K+ Conduction and Selectivity," Science 280(5360): 69-77.
Elwenspoek et al. (1998) "14.4.5 Radical depletion in a trench," Silicon Micromachining, Cambridge Univ. Press: Cambridge, England:352-356.
Ganguli, S. et al. (1997) "Improved growth and thermal stability of Parylene films," J. Vac. Sci. Technol. A, 15(6):3138-3142.
Gao, H. et al. (2003) "Spontaneous Insertion of DNA Oligonucleotides into Carbon Nanotubes," Nano Letters 3(4):471-473.
Harrell, C.C. et al. (2003) "Synthetic Single-Nanopore and Nanotube Membranes," Anal. Chem. 75:6861-6867.
Hata, K. et al. (2004) "Water-Assisted Highly Efficient Synthesis of Impurity-Free Single-Walled Carbon Nanotubes," Science 306:1362-1364.
Hinds, B.J. et al. (2004) "Aligned Multiwalled Carbon Nanotube Membranes," Science 303(5654):62-65.
Holt, J.K. et al. (2004) "Fabrication of a Carbon Nanotube-Embedded Silicon Nitride Membrane for Studies of Nanometer-Scale Mass Transport," Nano Letters 4(11):2245-2250.
Holt, J.K. et al. (2006) "Fast Mass Transport Through Sub-2-Nanometer Carbon Nanotubes," Science 312(5776):1034-1037.
Hou, H. et al. (2002) "Poly(p-xylylene) Nanotubes by Coating and Removal of Ultrathin Polymer Template Fibers," Macromolecules 35:2429-2431.
Hummer, G. (2007) "Water, proton, and ion transport: from nanotubes to proteins," Molecular Physic 105(2):201-207.
Hummer, G. et al. (2001) "Water conduction through the hydrophobic channel of a carbon nanotube," Nature 414(6860):188-190.
Iijima, S. et al. (1996) "Structural flexibility of carbon nanotubes," J. Chem. Phys. 104(5):2089-2092.
International Search Report for International Application No. PCT/US2009/045675, mailed Jan. 15, 2010, 2 pages.
Itaya, K. et al. (1984) "Properties of Porous Anodic Aluminum Oxide Films as Membranes," J. Chem. Eng. Jpn. 17(5):514-520.
Jiang, Y.X. et al. (2002) "Crystal structure and mechanism of a calcium-gated potassium channel," Nature 417(6888):515-522.
Jiang, Y.X. et al. (2002) "The open pore conformation of potassium channels," Nature 417:523-526.
Joseph, S. et al. (2003) "Electrolytic Transport in Modified Carbon Nanotubes," Nano Letters 3(10):1399-1403.
Kalra, A. et al. (2003) "Osmotic water transport through carbon nanotube membranes," Proc Natl Acad Sci USA 100(18):10175-10180.
Koga, K. et al. (2001) "Formation of ordered ice nanotubes inside carbon nanotubes," Nature 412:802-805.
Kolesnikov, A.I. et al. (2004) "Anomalously Soft Dynamics of Water in a Nanotube: A Revelation of Nanoscale Confinement," Phys. Rev. Lett. 93:035503-1-035503-4.
Kotsalis, E.M. et al. (2004) "Multiphase water flow inside carbon nanotubes," Int. J. Multiphase Flow 30:995-1010.
Kronengold, J. et al. (2003) "Single-channel SCAM Identifies Pore-lining Residues in the First Extracellular Loop and First Transmembrane Domains of Cx46 Hemichannels," J Gen Physiol. 122(4):389-405.

Kumar, P. et al. (2008) "Polyethyleneimine-Modified MCM-48 Membranes: Effect of Water Vapor and Feed Concentration on $N_2/CO_2$ Selectivity" Ind. Eng. Chem. Res. 47:201-208.
Kuo, A.L. et al. (2003) "Crystal Structure of the Potassium Channel KirBac1.1 in the Closed State," Science 300(5627):1922-1926.
Lai, Z. et al. (2003) "Microstructural Optimization of a Zeolite Membrane for Organic Vapor Separation," Science 300:456-460.
Leger, C. et al. (1996) "Preparation and properties of surface modified ceramic membranes. Part III. Gas permeation of 5 nm alumina membranes modified by trichloro-octadecylsilane," J. Memb. Sci. (120):187-195.
Leung, K. et al. (2006) "Salt Permeation and Exclusion in Hydroxylated and Functionalized Silica Pores," Phys. Rev. Lett. 96(9):4.
Li, J. et al. (1999) "Highly-ordered carbon nanotube arrays for electronics applications," Appl. Phys Lett. 75(3):367-369.
Li, P.H. et al. (2007) "Tailoring Wettability Change on Aligned and Patterned Carbon Nanotube Films for Selective Assembly," J Phys Chem B. 111(7):1672-1678.
Liu, H. et al. (2006) "Ion permeation dynamics in carbon nanotubes," J. Chem. Phys. 125:084713-1084713-14.
Lindsay, R.S. et al. (2003)"Test Results of Air-Permeable Charcoal Impregnated Suits to Challenge by Chemical and Biological Warfare Agents and Simulants: Summary Report", U.S. Amy Soldier and Biological Chemical Command Report, ECBC-TR, Aberdeen Proving Ground, MD, Unclassified Report.
Liu, H. et al. (2006) "Ion permeation dynamics in carbon nanotubes," J. Chem. Phys. 125:084713-1-084713-14.
Ma, R.Z. et al. (1998) "Processing and properties of carbon nanotubes-nano-SiC ceramic," J. Mater. Sci. 33:5243-5246.
Majumder, M. et al. (2005) "Effect of Tip Functionalization on Transport through Vertically Oriented Carbon Nanotube Membranes," J Am Chem Soc. 127(25): 9062-9070.
Majumder, M. et al. (2005) "Nanoscale hydrodynamics: Enhanced flow in carbon nanotubes," Nature 438(7064): 44.
Majumder, M. et al. (2007) "Voltage gated carbon nanotube membranes," Langmuir 23(16): 8624-8631.
Melechko, A.V. et al. (2005) "Vertically aligned carbon nanofibers and related structures: Controlled synthesis and directed assembly," Applied Physics Reviews 97: 041301-1-041301-39.
Miyazawa, A. et al. (2003) "Structure and gating mechanism of the acetylcholine receptor pore," Nature 423:949-955.
Murakami, Y. et al. (2004) "Growth of vertically aligned single-walled carbon nanotube films on quartz substrates and their optical anisotropy," Chem. Phys. Lett. 385:298-303.
Murata, K. et al. (2000) "Structural determinants of water permeation through aquaporin-1," Nature 407:599-605.
Nagai, Y. et al. (2006) "Slow release of molecules in self assembling peptide nanofiber scaffold," Journal of Controlled Release 115(1):18-25.
Naguib, N. et al.(2004) "Observation of Water Confined in Nanometer Channels of Closed Carbon Nanotubes," Nano Lett. 4(11):2237-2243.
Nednoor, P. et al. (2007) "Carbon nanotube based biomimetic membranes: mimicking protein channels regulated by phosphorylation," J. Mater. Chem. 17:1755-1757.
Nednoor, P. et al. (2005) "Reversible Biochemical Switching of Ionic Transport through Aligned Carbon Nanotube Membranes," J. Chem. Mater. 17:3595-3599.
Nightingale, E.R. (1959) "Phenomenological theory of ion solvation—Effective radii of hydrated ions," Journal of Physical Chemistry 63(9):1381-1387.
Park, J.H. et al. (2006) "Ion separation using a Y-junction carbon nanotube," Nanotechnology 17: 895-900.
Peter, C. et al. (2005) "Ion Transport through Membrane-Spanning Nanopores Studied by Molecular Dynamics Simulations and Continuum Electrostatics Calculations," Biophys 89(4): 2222-2234.
Robertson, J.K. et al. (1994) "A Nested Electrostatically-Actuated Microvalve for an Integrated Microflow Controller," Proc. IEEE Micro Electro Mechanical Systems: 7-12.
Robertson, J.K. et al. (2001) "Modeling a microfluidic system using Knudsen's empirical equation for flow in the transition regime," J. Vac. Sci. Technol. A 19(1):358-364.

(56) References Cited

OTHER PUBLICATIONS

Roehl, J.E. et al. (2000) "Residual Life Indicators—Point Chemical Detectors Used to Measure the Capacity of Activated Carbon in Protective Garments, Gas Mask Filters, and Collective Protection Filters," Scentczar Corporation Report, 10/23-27:123-130.
Rogojevic, S. et al. (1999) "Modeling vapor deposition of low-$K$ polymers: Parylene and polynaphthalene," J. Vac. Sci. Technol. 17(1):266-2743.
Rousseau, R. et al. (2004) "Modeling protonated water networks in bacteriorhodopsin," Phys. Chem. Chem. Phys. 6:1848-1859.
Rutherford, S.W. et al. (1997) "Review of Time Lag Permeation Technique as a Method for Characterisation of Porous Media and Membranes," Adsorption 3:283-312.
Sakamoto, Y. et al. (2007) "Preparation and CO2 separation properties of amine-modified mesoporous silica membranes," Microporous and Mesoporous Materials 101(1-2):303-311.
Schaep, J. et al. (1998) "Influence of ion size and charge in nanofiltration," Separation and Purification Technology 14(1-3):155-162.
Schaep, J. et al. (2001) "Modelling the retention of ionic components for different nanofiltration membranes," Separation and Purification Technology 22-23:169-179.
Skoulidas, A.I. et al. (2002) "Rapid Transport of Gases in Carbon Nanotubes," Phys. Rev. Lett. 89(18):185901-1-185901-4.
Sui, H.X. et al. (2001) "Structural basis of water-specific transport through the AQP1 water channel," Nature 414(6866):872-878.
Sumikama, T. et al. (2006) "Mechanism of ion permeation in a model channel: Free energy surface and dynamics of K+ ion transport in an anion-doped carbon nanotube, " J Phys Chem B. 110(41):20671-20677.
Sun, L. et al. (2000) "Single Carbon Nanotube Membranes: A Well-Defined Model for Studying Mass Transport through Nanoporous Materials," J. Am. Chem. Soc. 122:12340-12345.
Tong, H.D. et al. (2004) "Silicon Nitride Nanosieve Membrane," Nano. Lett. 4(2):283-287.
Trexler, E.B. et al. (2000) "The First Extracellular Loop Domain Is a Major Determinant of Charge Selectivity in Connexin46 Channels," Biophys J. 79(6):3036-3051.
Van Rijn, C.J.M. et al. (1995) "Micro filtration Membrane Sieve with Silicon Micro Machining for Industrial and Biomedical Applications," IEEE Conf. MEMBS '95:83-87.
Van Rijn, C. et al. (1997)"Deflection and Maximum Load of Microfiltration Membrane Sieves Made with Silicon Micromachining," J. Microelectromech. Syst. 6(1):48-54.
Vezenov, D.V. et al. (1997) "Force titrations and ionization state sensitive imaging of functional groups in aqueous solutions by chemical force microscopy," J. Am. Chem. Soc. 119: 2006-2015.
Weston, A et. al. (1992) "Effect of electrolyte-composition on the separation of inorganic metal cations by capillary ion electrophoresis," Journal of Chromatography 602(1-2):249-256.
Weston, A. et. al. (1992) "Factors affecting the separation of inorganic metal-cations by capillary ectrophoresis," Journal of Chromatography 593(1-2):289-295.
Wikstrom, M. (2003) "Water-gated mechanism of proton translocation by cytochrome c oxidase," Biochim Biophys Acta.-Bioenergetics 1604(2): 61-65.
Wikstrom, M. (1998) "Proton translocation by bacteriorhodopsin and heme-copper oxidases," Curr Opin Struct Biol 8(4):480-488.
Williams, M.E. et al. (1999) "Separation of Organic Pollutants by Reverse Osmosis and Nanofiltration Membranes: Mathematical Models and Experimental Verification," Ind. Eng. Chem. Res. 38(10):3683-3695.
Wong, S.S. et al. (1998) "Covalently Functionalized Nanotubes as Nanometer-Sized Probes in Chemistry and Biology," Nature 394:52-55.
Wong, S.S. et al. (1998) "Covalently-Functionalized Single-Walled Carbon Nanotube Probe Tips for Chemical Force Microscopy," J. Am. Chem. Soc. 120:8557-8558.
Yang, D.Q. et al. (2005) "Controlled chemical functionalization of multiwalled carbon nanotubes by kiloelectronvolt argon ion treatment and air exposure," Langmuir. 21(18):8539-8545.
Yaroshchuk, A.E. (2001) "Non steric mechanisms of nano- filtration: superposition of Donnan and dielectric exclusion," Sep. and Purification Technol. 22-23:143-158.
Yu, M. et al. (2005) "Interphase exchange coupling in Fe/Sm-Co bilayers with gradient Fe thickness," J. Appl. Phys. 98:063908-1-06908-4.
Zhu, J. et al. (2002) "Density-Induced Interchange of Anisotropy Axes at Half-Filled High Landau Levels," Phys. Rev. Lett. 88(11):116803-1-116803-4.
Non-Final Office Action dated Mar. 5, 2013, U.S. Appl. No. 12/955,843, 9 pages.
Notice of Allowance dated May 25, 2011, U.S. Appl. No. 12/064,604, 11 pages.
Non-Final Office Action dated Dec. 8, 2010, U.S. Appl. No. 12/064,604, 9 pages.
Non-Final Office Action dated Jun. 29, 2010, U.S. Appl. No. 12/064,604, 11 pages.

* cited by examiner

FIG. 10A  FIG. 10B
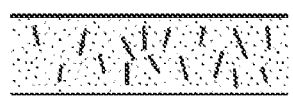
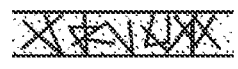
FIG. 10C  FIG. 10D

MEMBRANES WITH FUNCTIONALIZED CARBON NANOTUBE PORES FOR SELECTIVE TRANSPORT

CROSS REFERENCE TO RELATED APPLICATIONS

This application is a national stage application under 35 U.S.C. §371 of International Application No. PCT/US2009/045675, filed May. 29, 2009, which in turn claims priority under 35 U.S.C. §119 (e) of U.S. Provisional Application No. 61/056,940, filed on May. 29, 2008, the contents of each of which are hereby incorporated by reference in their entirety.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

Provided herein are carbon nanotubes membranes and nanofiltration membranes whose through-pores are made of sub-6 nm carbon nanotubes with entrance modified by functional groups. Charges at the pore entrance and the small diameter of the pores ensures that these membranes are able to efficiently exclude ions and small molecules while maintaining ultra-fast fluid permeation.

BACKGROUND OF THE INVENTION

Ion transport across cellular membranes is essential to many of life's processes, such as electrical signaling in nerves, muscles, and synapses or cell's maintenance of homeostatic balance. Biological systems achieve rapid, selective and ultra-efficient trans-membrane mass transport by employing a large variety of specialized protein channels of nanometer or subnanometer size (Hille B (2001) *Ion Channel of Excitable Membranes* (Sinauer Associates, Inc., Sunderland)). High resolution x-ray structures, protein sequencing, targeted mutations, and biophysical characterizations have provided new insights on the link between nanochannel protein architecture, transport rates, selectivity, and gating properties.

Interestingly, these studies have shown that membrane nanochannels share several common features. For example, aquaporins (Sui H X, Han B G, Lee J K, Walian P, Jap B K (2001) Structural basis of water-specific transport through the AQP1 water channel. *Nature* 414:872-878; and Murata K, Mitsuoka K, Hirai T, Walz T, Agre P, Heymann J B, Engel A, Fujiyoshi Y (2000) Structural determinants of water permeation through aquaporin-1. *Nature* 407:599-605), proton (Wikstrom M (1998) Proton translocation by bacteriorhodopsin and heme-copper oxidases. *Curr Optin Struct Biol* 8:480-488, Wikstrom M, Verkhovsky M I, Hummer G (2003) Water-gated mechanism of proton translocation by cytochrome c oxidase. *BBA-Bioenergetics* 1604:61-65), and ion channels (Jiang Y X, Lee A, Chen J Y, Cadene M, Chait B T, MacKinnon R (2002) Crystal structure and mechanism of a calcium-gated potassium channel. *Nature* 417:515-522; Jiang Y X, Lee A, Chen J Y, Cadene M, Chair B T, MacKinnon R (2002) The open pore conformation of potassium channels. *Nature* 417:523-526; Bass R B, Strop P, Barclay M, Rees D C (2002) Crystal structure of *Escherichia coli* MscS, a voltage-modulated and mechanosensitive channel. *Science* 298:1582-1587; Doyle D A, Cabral J M, Pfuetzner R A, Kuo A L, Gulbis J M, Cohen S L, Chait B T, MacKinnon R (1998) The structure of the potassium channel: Molecular basis of K+ conduction and selectivity. *Science* 280:69-77; Miyazawa A, Fujiyoshi Y, Unwin N (2003) Structure and gating mechanism of the acetylcholine receptor pore. *Nature* 423:949-955; and Kuo A L, Gulbis J M, Antcliff J F, Rahman T, Love E D, Zimmer J, Cuthbertson J, Ashcroft F M, Ezaki T, Doyle D A (2003) Crystal structure of the potassium channel KirBacl.1 in the closed state. *Science* 300:1922-1926) all have relatively narrow and hydrophobic pore regions. By contrast, the selectivity filter regions of membrane ion channels are enriched with charged residues.

Despite progress made in recent decades, the complex macromolecular nature of these biological machines still complicates the understanding of the underlying mechanisms responsible for fast mass transport, selectivity, gating, and the functional role of hydrophobic pore lining and charged functionalities. Thus, it is desirable to create simplified, biomimetic nanochannels that could help to clarify the physics of ion permeation at the nanoscale, as well as create the next generation of membranes that employ efficient molecular transport for applications ranging from water purification to separations of biomolecules. Recent theoretical and experimental works have proposed carbon nanotubes (CNTs) as candidates for such simplified models of biological channels. The graphite walls of CNTs form hydrophobic pores with diameters close to those of biological channels.

Molecular dynamics (MD) and theoretical studies have shown single-file transport for water along the nanotube axis (Berezhkovskii A, Hummer G (2002) Single-file transport of water molecules through a carbon nanotube. *Phys Rev Lett* 89:4; Hummer G, Rasaiah J C, Noworyta J P (2001) Water conduction through the hydrophobic channel of a carbon nanotube. *Nature* 414:188-190; Hummer G (2007) Water, proton, and ion transport: from nanotubes to proteins. *Mol Phys* 105:201-207; and Kalra A, Garde S, Hummer G (2003) Osmotic water transport through carbon nanotube membranes. *Proc Natl Acad Sci USA* 100:10175-10180) that is reminiscent of the water wires observed in aquaporins (Sui H X, Han B G, Lee J K, Walian P, Jap B K (2001) Structural basis of water-specific transport through the AQP1 water channel. *Nature* 414:872-878; and Murata K, Mitsuoka K, Hirai T, Walz T, Agre P, Heymann J B, Engel A, Fujiyoshi Y (2000) Structural determinants of water permeation through aquaporin-1. *Nature* 407:599-605). Predicted (Hummer G, Rasaiah J C, Noworyta J P (2001) Water conduction through the hydrophobic channel of a carbon nanotube. *Nature* 414:188-190; Hummer G (2007) Water, proton, and ion transport: from nanotubes to proteins. *Mol Phys* 105:201-207; and Kalra A, Garde S, Hummer G (2003) Osmotic water transport through carbon nanotube membranes. *Proc Natl Acad Sci USA* 100:10175-10180) and experimentally measured (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312:1034-1037; and Majumder M, Chopra N, Andrews R, Hinds B J (2005) Nanoscale hydrodynamics—Enhanced flow in carbon nanotubes. *Nature* 438:44-44) water transport rates through CNTs are extremely large and comparable to measured values for aquaporins. MD simulations have revealed the water ordering near the smooth hydrophobic walls to facilitate enhanced, frictionless water transport.

In addition, chemical inertness of the carbon nanotube sidewalls facilitate specific functionalization of the CNT pore entrance with different functionalities. This specificity provides an opportunity to create an artificial "selectivity filter" that could impart gating properties to a CNT (Hinds B J, Chopra N, Rantell T, Andrews R, Gavalas V, Bachas L G (2004) Aligned multiwalled carbon nanotube membranes. *Science* 303:62-65; Majumder M, Chopra N, Hinds B J (2005) Effect of tip functionalization on transport through vertically oriented carbon nanotube membranes. *J Am Chem Soc* 127:9062-9070; Majumder M, Zhan X, Andrews R, Hinds B J (2007) Voltage gated carbon nanotube membranes. *Langmuir* 23:8624-8631; Nednoor P, Chopra N, Gavalas V, Bachas L G, Hinds B J (2005) Reversible biochemical switching of ionic transport through aligned carbon nanotube membranes. *Chem Mater* 17:3595-3599; Nednoor P, Gavalas V G, Chopra N, Hinds B J, Bachas L G (2007) Carbon nanotube based biomimetic membranes: Mimicking protein channels regulated by phosphorylation. *J Mater Chem* 17:1755-1757; and Chopra N, Majumder M, Hinds B J (2005) Bifunctional carbon nanotubes by sidewall protection. *Adv Funct Mater* 15:858-864).

Reverse osmosis (RO) is currently a method for desalination of sea water. Sea water is an abundant reservoir of elemental water on Earth and as such is one of the important potential sources of fresh water that may be necessary for normal society functioning. Seawater has high salinity, which makes it unsuitable for most of human use, therefore seawater needs to be separated from its salt content in the desalination process.

In a typical RO desalination process, an applied pressure in excess of the osmotic pressure of the salt solution forces the solution through a semipermeable membrane that allows permeation of water while retaining the dissolved ions. This process requires high pressure on the high concentration side of the membrane, ranging from ~15 bar for brackish water to ~60 bar for seawater. Fresh water then collects on the downstream side of the membrane and the concentrated brine from the upstream side of the membrane is then discarded.

Current membranes used for RO desalination are based on cellulose acetate or aromatic polyamide polymers and present a thin dense barrier layer in the polymer matrix where most separation occurs. Since the barrier layer is effectively non-porous, the transport of water through the membrane occurs at low rates through a "solution-diffusion" mechanism: water absorbs on the upstream side of the membrane, diffuses down the chemical potential gradient (largely due to pressure gradient), and desorbs downstream. Salt transport occurs in a similar fashion; however, the driving force for transport is mainly the concentration gradient and the salt flux is insensitive to the pressure gradient. Thus, to achieve good water fluxes and high salt rejection, a very large applied pressure is required. As a consequence, the energy cost associated to the separation process is large. Also, these membranes may tend to foul easily.

Biological pores regulate the cellular traffic of a large variety of solutes, often with high selectivity and fast flow rates. These pores share several common structural features: the inner surface of the pore is frequently lined with hydrophobic residues and the selectivity filter regions often contain charged functional groups. Hydrophobic, narrow diameter carbon nanotubes can provide a simplified model of membrane channels by reproducing these critical features in a simpler and more robust platform. Previous studies demonstrated that carbon nanotube pores can support a water flux comparable to natural aquaporin channels.

SUMMARY OF THE INVENTION

Provided herein are sub-6-nm, aligned carbon nanotube membrane nanofluidic platform for selective transport through the pores of the nanotubes. In some embodiments, negatively charged groups are introduced at the opening of the carbon nanotubes by plasma treatment. In some embodiments, positively charged groups are introduced at the opening of the carbon nanotubes by chemical modification.

In one aspect, there is provided an array of carbon nanotubes functionalized on at least one end of at least one of the nanotubes, wherein the nanotubes have average pore size of less than 6 nm or less.

In another aspect, there is provided a membrane for enhanced fluid transport comprising, consisting essentially of, or consisting of an array of carbon nanotubes functionalized on at least one end of at least one of the nanotubes, wherein the nanotubes have average pore size of less than 6 nm or less and a matrix material disposed between the carbon nanotubes.

In another aspect, there is provided a membrane for an enhanced transport of desalted water from salted water comprising, consisting essentially of, or consisting of: a substantially vertically-aligned array of carbon nanotubes, wherein the nanotubes have average pore size of about 1-2 nm having at least one functionalized nanotube and a matrix material disposed between the carbon nanotubes.

In yet another aspect, there is provided a membrane for an enhanced transport of desalted water from salted water comprising, consisting essentially of, or consisting of: a substantially vertically-aligned array of carbon nanotubes, wherein the nanotubes have average pore size of about 1-2 nm with a charge density of about 1-3 mM and have at least one functionalized nanotube; and a matrix material disposed between the carbon nanotubes.

In yet another aspect, there is provided a chip comprising, consisting essentially of, or consisting of a plurality of membranes, as defined herein.

In yet another aspect, there is provided a method of separating an analyte from a fluid by passing the fluid containing the analyte through the carbon nanotubes or the membranes comprising, consisting essentially of, or consisting of the carbon nanotubes or the membranes, as defined herein.

BRIEF DESCRIPTION OF THE DRAWINGS

This invention will be further described with reference being made to the accompanying drawings.

FIG. 10 illustrates various embodiments of the membrane structure of the invention.

DETAILED DESCRIPTION OF THE INVENTION

1. Definitions

Figure 1:
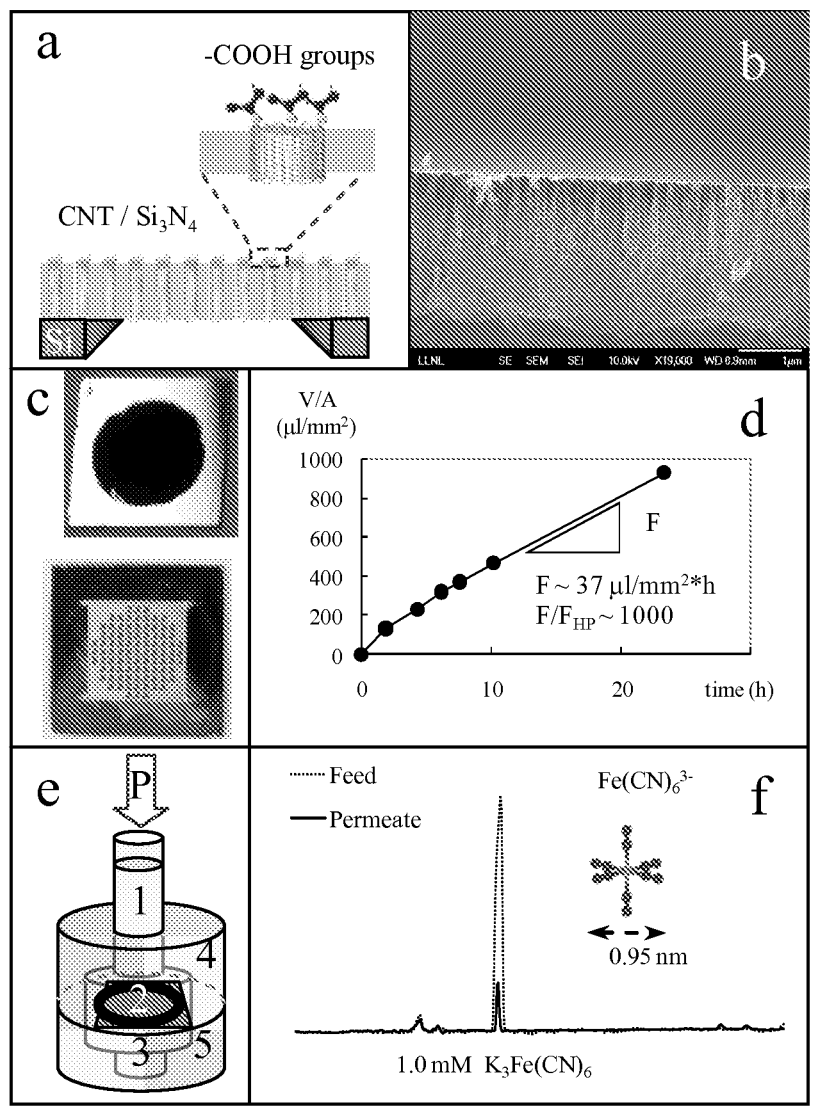
FIG. 1 illustrates (a) Cross section schematic of a CNT membrane representing the silicon support chip, the aligned DWNTs, the filling silicon nitride matrix, and the CNT tips functionalized with carboxylic groups. (b) Cross section SEM image of the CNT/silicon nitride composite showing the gap-free coating of silicon nitride. (c) Photographs of the membrane sides exposed to the feed (top) and to the permeate (bottom). (d) Time variation of permeate volume per unit area of freestanding membrane during the filtration of 0.6 mM $K_3Fe(CN)_6$ solution. The resulting permeation flux, F, is ~1000 larger than the calculated value with the Hagen-Poiseuille equation, $F_{HP}$. (e) Schematic of the nanofiltration cell showing the column of feed solution (1) pressurized at P=0.69 bar, the CNT membrane (2), the permeate solution (3), feed (4) and permeate (5) chambers. (f) Capillary electrophoresis chromatogram for feed (dotted line) and permeate (solid line) showing a 91% exclusion of the ferricyanide anion after nanofiltration of a 1.0 mM $K_3Fe(CN)_6$ solution.

Before the present compositions, and methods are described, it is to be understood that the invention is not limited to the particular methodologies, protocols, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All technical and patent publications cited herein are incorporated herein by reference in their entirety. Nothing herein is to be construed as an admission that the invention is not entitled to antedate such disclosure by virtue of prior invention.

In accordance with the present invention and as used herein, the following terms are defined with the following meanings, unless explicitly stated otherwise.

As used in the specification and claims, the singular form "a", "an" and "the" include plural references unless the context clearly dictates otherwise.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about". It also is to be understood, although not always explicitly stated, that the reagents described herein are merely exemplary and that equivalents of such are known in the art.

As used herein, the term "acidic group" refers to the group which donates a hydrogen ion to the base or which when dissolved in water gives a solution with hydrogen ion activity greater than pure water, i.e., a pH less than 7.0. The acidic groups are negatively charged groups at pH higher than 7.0.

As used herein, the term "amide" refers to —$CONH_2$ group.

As used herein, the term "amine" refers to —$NH_2$ group.

As used herein, the term "array" refers to a group of carbon nanotubes with same attributes as the individual carbon nanotube.

As used herein, the term "basic group" refers to the group which accepts a hydrogen ion or which when dissolved in water gives a solution with pH greater than 7.0. The basic groups are positively charged groups at pH lower than 7.0.

As used herein, the term "carboxylic acid" refers to —COOH group.

As used herein, the term "comprising" or "comprises" is intended to mean that the devices and methods include the recited elements, but not excluding others. "Consisting essentially of" when used to define devices, methods, or kit of parts, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace amount of elements of other ingredients and substantial method steps. Embodiments defined by each of these transition terms are within the scope of this invention.

As used herein, the term "dendrimer" refers to repeatedly branched molecules. Dendritic molecules are repeatedly branched species that are characterized by their structure perfection. The latter is based on the evaluation of both symmetry and polydispersity. The area of dendritic molecules can roughly be divided into the low-molecular weight and the high-molecular weight species. The first category includes dendrimers and dendrons whereas the second encompasses dendronized polymers, hyperbranched polymers, and brush-polymers (also called bottle-brushes). Dendrimers and dendrons are repeatedly branched, monodisperse, and usually highly symmetric compounds. There is no apparent difference in defining dendrimer and dendron. A dendron usually contains a single chemically addressable group that is called the focal point. Because of the lack of the molar mass distribution high-molar-mass dendrimers and dendrons are macromolecules but not polymers. The properties of dendrimers are dominated by the functional groups on the molecular surface. Dendritic encapsulation of functional molecules allows for the isolation of the active site, a structure that mimics the structure of active sites in biomaterials because dendritic scaffolds separate internal and external functions. For example, a dendrimer can be water-soluble when its end-group is a hydrophilic group, like a carboxyl group.

As used herein, the term "desalted water" refers to water from which salt has been substantially removed.

As used herein, the term "fluid" refers to both gas as well as liquid.

As used herein, the terms "functional," or "functionalized," or "functionalization," refer to any group that imparts selectivity to the carbon nanotubes in transporting fluids. The functional groups include, without limitation, charged groups, non-charged groups, or permanent charged groups.

As used herein, the term "liquid" refers to any liquid that has the particles loose and can freely form a distinct surface at the boundaries of its bulk material. Examples of liquid include, but are not limited to, water, industrial streams, chemicals, or bodily liquids. Examples of water include, without limitation, salted water, sea water, well water, underground water, and waste water. Examples of industrial stream include, without limitation, pharmaceutical industry process stream, or food industry process stream. Examples of chemicals include, without limitation, chemicals used in pharmaceutical industry, laboratories, or research organizations. Examples of bodily liquids include, without limitation, diluted, untreated, or treated body fluids such as milk, blood, plasma, urine, amniotic liquid, sweat, saliva, etc.

As used herein, the term "membrane" intends a porous material whose lateral dimension is significantly larger than the dimensions across it.

As used herein the term "nanotube" intends a substantially cylindrical tubular structure of which the most inner diameter size is an average of less than about 6 nm. Nanotubes are typically, but not exclusively, carbon molecules and have novel properties that make them potentially useful in a wide variety of applications in nanotechnology, electronics, optics, and other fields of materials science. They exhibit extraordinary strength and unique electrical properties, and are efficient conductors of heat. The nanotube is a member of the fullerene structural family, which also includes buckyballs. Where buckyballs are spherical in shape, a nanotube is cylindrical, with at least one end typically capped with a hemisphere of the buckyball structure. The name is derived from their size, since the diameter of a nanotube can be on the order of a few nanometers (approximately 50,000 times smaller than the width of a human hair), while they can be up to several millimeters in length. The nanotubes can be single-walled nanotubes (SWNTs), double-walled nanotubes (DWNTs) and multi-walled nanotubes (MWNTs). Nanotubes may be composed primarily or entirely of $sp^2$ bonds, similar to those of graphite. This bonding structure, stronger than the $sp^3$ bonds found in diamond, provides the molecules with their unique strength. Nanotubes naturally align themselves into "ropes" held together by Van der Waals forces. Under high pressure, nanotubes can merge together, trading some $sp^2$ bonds for $sp^3$ bonds, giving great possibility for producing strong, unlimited-length wires through high-pressure nanotube linking.

Nanotubes are comprised of various materials, which include but are not limited to carbon, silicon, silica and selenium. Inorganic nanotubes such as boron nitride have also been synthesized. Carbon nanotubes include single wall, double wall, and multiwall types. A "single-wall" is one tubular layer, straight or tortuous, of carbon atoms with or without a cap at the ends, while a "double-wall" is two concentric tubular layers, straight or tortuous, of carbon atoms with or without a cap at the ends and a "multi-wall" intends more than two concentric tubular layers, straight or tortuous, of carbon atoms with or without a cap at the ends.

The nanotubes can be arranged in an array wherein a plurality of nanotubes are organized in spatial arrangement with each other. For example, they can be aligned substantially parallel to each other as "substantially vertically aligned" and be generally or substantially perpendicular to a substrate. Nanotubes can be grown off of surfaces that have catalyst particles disposed on the surface in an ordered or disordered array.

As used herein, the term "non-charged group" refers to the group that has no positive or negative charge on it.

As used herein, the term "permanent charged group" refers to the group which has the charge not dependent on the surrounding pH. For example, quartenary ammonium ion has a positive charge.

As used herein, the term "polymer" is a large molecule (macromolecule) composed of repeating structural units typically connected by covalent chemical bonds. Examples of polymer include, but are not limited to, linear and branched polyethylene glycol (PEG), polyamides, polyesters, polyimides and polyurethanes. Examples of polyamides include, but are not limited to, nylon 6; nylon 6,6; and nylon 6,12. Examples of polyesters include, but are not limited to, poly (ethylene terephthalate), poly(trimethylene terephthalate), and poly(trimethylene naphthalate).

As used herein, the term "polyelectrolyte" refers to polymers whose repeating units bear an electrolyte group. These groups will dissociate in aqueous solutions (water), making the polymers charged. Polyelectrolyte properties are thus similar to both electrolytes (salts) and polymers (high molecular weight compounds), and are sometimes called polysalts. Like salts, their solutions are electrically conductive. Like polymers, their solutions are often viscous. Charged molecular chains, commonly present in soft matter systems, play a role in determining structure, stability and the interactions of various molecular assemblies. One of the role of polyelectrolytes is in biology and biochemistry. Many biological molecules are polyelectrolytes. For instance, polypeptides (thus all proteins), and polynucleotides such as DNA, and RNA are polyelectrolytes including both natural and synthetic polyelectrolytes. Other examples of polyelectrolytes include, without limitation, polysterenesulfonate (PSS).

As used herein, the term "salted water" refers to water with salt ($Na^+Cl^-$) in it. The salted water can be sea water. Along with $Na^+$ and $Cl^-$ ions, the salted water can contain one or more of additional ions. Examples of ions include, but are not limited to, magnesium, sulfur, calcium, potassium, strontium, barium, radium, bromine, etc.

As used herein, the term "substantially" refers to more than about 50%.

As used herein, the term "transport" refers to separation as well as filtration of the fluid.

2. Carbon Nanotubes

The various embodiments described herein include carbon nanotubes, membranes, fabric, articles and devices comprising, consisting essentially of, or consisting of membranes, and methods of making these membranes, fabric, articles, and devices. In one aspect, the membranes surprisingly provide faster than expected and thus efficient liquid and gaseous fluid transport despite nanoscale pore size. Moreover, they are mechanically robust, and they provide a versatile system to commercialize fluid transport for particular applications.

In one aspect, there is provided an array of carbon nanotubes functionalized on at least one end of at least one of the nanotubes, wherein the nanotubes have average pore size less than about 6 nm or less as described herein.

Also provided herein are carbon nanotubes and nanofiltration membranes whose through-pores are made of sub-6 nm carbon nanotubes with at least one end or the pore entrance of at least one of the nanotube modified by functional groups. The functional groups can be charged groups or uncharged groups. These carbon nanotube membranes exhibit high permeability since water and gas flow through carbon nanotubes is orders of magnitude faster than through other pores with the same or smaller diameter.

The charged groups at the pore entrance and/or the small diameter of the pores causes these membranes to be able to efficiently exclude ions while maintaining ultra fast water permeation. Negatively charged groups provide rejection for anions and can be introduced at the opening of the carbon nanotubes by plasma treatment. Positively charged groups provide rejection for cations and can be introduced by chemical modification. Rejection depends on electrostatic action between the membrane and ions in solution.

The carbon nanotubes are aligned or not aligned and are embedded in a ceramic or in a polymeric matrix that fills the spaces between carbon nanotubes. In some embodiments, the carbon nanotubes are single wall, double-wall nanotubes, or multi-wall nanotubes. In some embodiments, substantially all of the nanotubes of the array are substantially vertically-aligned. In some embodiments, more than about 50% of the nanotubes are vertically-aligned. In some embodiments, more than about 60%; more than about 70%; more than about 80%; more than about 90%; more than about 95%; or about 100% of the carbon nanotubes are vertically aligned.

The carbon nanotubes are opened at both ends and at least one end or the pore entrance of at least one of the nanotube is modified with functional groups.

The nanotube pore entrance can contain functional groups that change conformation or charge upon change in pH or change in temperature. The pH or temperature change can then trigger changes in membrane selectivity. An example of pH sensitive rejection is carboxylic group functionalization because carboxylic croup changes charge with the change of pH. An example for temperature-sensitive membrane-selectivity change is the use of hydrogen-bonded hairpin that can be broken up and reformed (for example a RNA hairpin). These embodiments will be provided in detail below.

In one embodiment of this invention, carboxylic groups are created on the carbon nanotube rim by the etching processes used for opening the carbon nanotubes and for removing the excess filling matrix eventually covering the tips. These etching processes include argon ion milling, reactive ion etching, oxygen plasma, water plasma, and air plasma. When in contact with an aqueous salt solution at a pH larger than the pKa of an acid, for example, carboxylic acid, these functional groups are ionized and form a rim of charges at the carbon nanotube entrance.

In some embodiments, the nanotube is functionalized with the same or different group. In some embodiments, the nanotube is functionalized with the same group. In some embodiments, the at least one end or the pore entrance of at least one of the nanotube is functionalized with a charged group. Examples of charged groups attached to the end or the pore entrance of the nanotube, include, but are not limited to, sulfonate, phosphonate, ammonium, carboxylate, etc. In some embodiments, the at least one end or the pore entrance of at least one of the nanotube is functionalized with a non-charged group. Example of non-charged group includes, but is not limited to, non-charged dendrimer.

In some embodiments, the nanotube is functionalized with an acidic group or a basic group. In some embodiments, the nanotube is functionalized with a permanent charged group. In some embodiments, the nanotube is functionalized with a group selected from carboxylic acid, sulfonic acid, phosphonic acid, amine, amide, polymer, dendrimer, and a polyelectrolyte. In some embodiments, the nanotube is functionalized with an amide or polyamide. In some embodiments, the nanotube is functionalized with a short oligomer or a long oligomer of, for example, polyethylene glycol (PEG) polymer. In some embodiments, the nanotube is functionalized with polyelectrolytes. In some embodiments, the nanotube is functionalized with a dendrimer. Example of dendrimer includes, without limitation, poly(amidoamine) (PAMAM).

The functionalization of the nanotubes enhances rejection of the ions in the fluid, enhances selectivity of the membranes, and/or reduces fouling of the membranes.

For carbon nanotube pores with sub-6 nm diameter, steric hindrance and/or electrostatic interactions between the charged functionalities on the membrane and ionic species in solution enable effective rejection of ions during salt solution filtration.

In some embodiments, the nanotube is functionalized with polymers, branched polymers, dendrimers, or poly(m-aminobenzene sulfonic acid). In some embodiments, the nanotube end or pore entrance is modified by attaching a short chain or long chain primary amine through an amide bond as shown below:

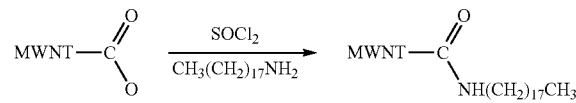

The multiwall nanotube in the above reaction is for illustration purposes only. It is to be understood that the reaction can be carried out with single-wall as well as double-wall nanotubes too.

Figure 8:
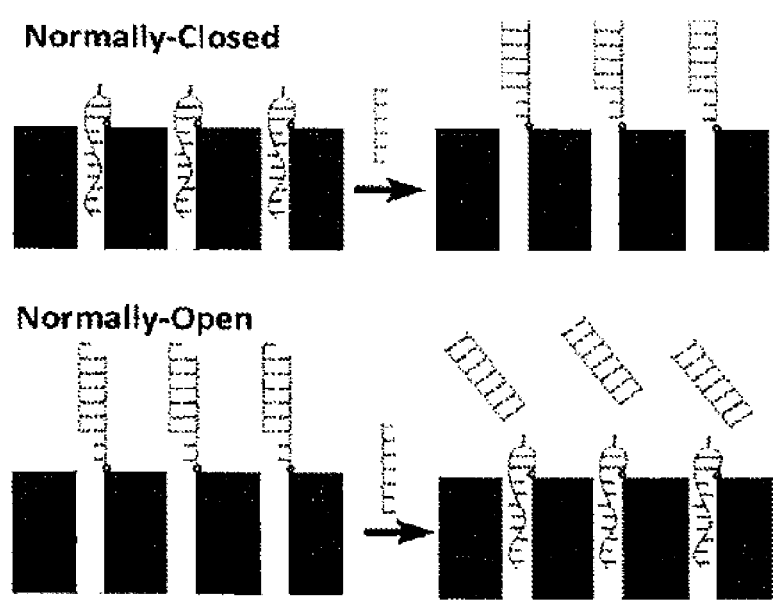
FIG. 8 illustrates DNA based programmable gating of CNT membranes.

In some embodiments, the nanotube is functionalized with a polyelectrolyte, such as a single stranded or double stranded DNA (deoxyribonucleic acid). DNA-based gating of nanotube membranes is based on attaching a short single-stranded DNA hairpin to the mouth of the CNT membrane pore. The ssDNA (single strand DNA) can (according to the MD simulations, H. Gao et al., *Nano Lett.* 3, 471 (2003)) spontaneously insert into the CNT pore channel. This invention can be realized in several configurations. An embodiment is as shown in FIG. 8. In the normally-closed configuration the mouth of the nanotube is blocked by a partially-inserted DNA hairpin attached to the nanotube mouth. Addition of a complementary DNA strand extracts the DNA strand from the channel and opens up the pore. In the normally-open configuration, the DNA hairpin is complexed with the slightly longer complementary DNA; addition of the reverse complementary sequence strips the complement off the hairpin and causes the hairpin to block the nanotube opening. The benefits of this approach include the ability to regulate the permeability of CNT membrane using very specific sequences of DNA. Possible uses of this embodiment range from timed delivery of reagents or drugs, to creation of "smart surfaces" that would release antibiotics, antidotes or other chemicals when triggered by presence of a specific pathogenic DNA sequence outside of the membrane.

In some embodiments, a short section of the carbon nanotube, embedded in a matrix, is removed at the entrance. That region of the matrix is modified to create a gate region. The walls of the pore formed in the matrix are used to anchor chemical groups allowing for control of the length of the gate region.

Figure 9A:
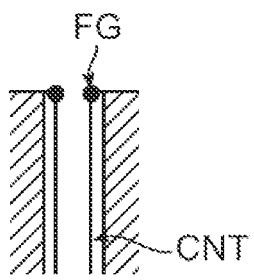
FIG. 9 illustrates CNT embodiments with functionalization of the end or the pore entrance of the CNT.
Figure 9B:
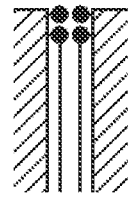
Figure 9C:
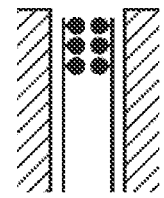

The at least one end or the pore entrance of at least one of the nanotubes can be functionalized in various ways, as depicted in FIG. 9. In some embodiments, the functional groups are attached to the end or tips of the CNTs (FIG. 9A). In some embodiments, CNTs are preferentially etched, leaving a pore of the matrix above it and the functional groups are attached to the sidewalls of the pore created in the polymer matrix (FIG. 9B). In some embodiments, the inner side walls of the CNTs are functionalized by breaking the carbon-carbon bonds and attaching functional groups, such as for example, amide groups or charged groups such as tertiary amine, etc. (FIG. 9C). In some embodiments, both the matrix surface and the CNT mouth are functionalized with the ion-rejecting compound or the charged group. In some embodiments, the nanotube mouth is functionalized with a charged group and the matrix surface is functionalized with the foulant-rejecting moiety (such as PEG) to create a dual-functionalized membrane.

In some embodiments, the functionalization of at least one end or pore entrance of at least one nanotube in the membrane provides selectivity to the membrane in terms of the nature of the ions that can be removed from the water. For example, the nanotube end functionalized with carboxylate anion will selectively reject anions from water and the nanotube end functionalized with an amino cation will selectively reject cations from the water.

In some embodiments, the membranes possess temporarily protected pores. For example, a group that closes CNT and is released by external stimulus is useful as a way to protect the inside of the CNT from being filled or damaged during membrane fabrication, storage and transportation. This kind of group protection can be realized using photo-cleavable ligands. Example of photo-cleavable ligand includes, but is not limited to, 4-t-butyl-α nitrobenzyl cleavable with UV light.

In each of the above embodiments, it should be understood, although not explicitly stated that the nanotubes are functionalized with from about 5%-100% of the site available for functionalization; from about 10%-90%; from about 25%-75%; from about 50%-75%; or from about 50%-100%. In some embodiments, functionalization of the nanotubes with just one functional group is sufficient to impart properties to the membrane. In some embodiments, all the available sites on the nanotubes are functionalized to impart properties to the nanotubes. In some embodiment, the functionalization of the nanotube in a membrane provides an enhanced selectivity in the transport of the fluid than a non-functionalized nanotube. In some embodiment, the functionalization of the nanotube in a membrane provides an enhanced rejection of the salt from a salted water than a non-functionalized nanotube.

In each of the above embodiments, it should be understood, although not explicitly stated that the average pore sizes of the carbon nanotube membranes can be for example about 0.5 nm to about 6 nm, or about 1 nm to about 2 nm. In one embodiment, they are on average less than about 6 nm, but still of sufficient internal diameter to allow gas and liquid molecules to pass through them. Thus, alternative embodiments include nanotubes having average pores sizes of less than about 6 nm, or alternatively, less than about 5 nm, or alternatively, less than about 4 nm, or alternatively, less than about 3 nm, or alternatively, less than about 2 nm, or alternatively, less than about 1 nm, or alternatively between about 0.5 nm and about 6 nm, or alternatively between about 1 nm and about 4 nm and yet further, between about 1 nm and about 3 nm or yet further, between about 0.5 nm and about 2 nm.

In each of the above embodiments, it should be understood, although not explicitly stated that the number of pores having the aforementioned pore sizes in the membrane can be from greater than about 40%, or alternatively greater than about 45%, or alternatively more than about 50%, or alternatively, more than about 55%, or alternatively, more than about 60%, or alternatively more than about 65%, or alternatively more than about 70%, or alternatively more than about 75%, or alternatively more than about 80%, or alternatively more than about 85%, or alternatively more than about 90% or alternatively, more than about 95%, each of the total number of pores in the membrane. Typically, pore size is determined by TEM (Transmission Electron Microscope) or Raman spectroscopy method, although other methods are known in the art.

The carbon nanotubes in the membrane can be substantially single walled nanotubes or alternatively double walled nanotubes or alternatively multiwalled nanotubes or yet further comprise a combination of any of single-, double- or multiwalled. An array of substantially any one type of carbon nanotube (e.g., single, double or multi) intends greater than about 70%, or 80%, or 90% of the nanotubes in the array are of that type.

In one embodiment, the nanotubes can have open ends on one side, or on each side of the membrane. Opening can be determined by for example fluid transport through the carbon nanotube as well as analytical methods such as nanoscale electron microscopy. Nanotubes can be used in applications such as composites or cold emitters wherein the nanotube is open on but one side or is open on neither side.

In some cases, carbon nanotubes can also comprise catalyst nanoparticles at one end. For the purpose of illustration only, catalyst nanoparticles include, but are not limited to pure or alloyed iron, cobalt, nickel, molybdenum and platinum. In one embodiment, more than 10%; more than 20%; more than 30%; more than 40%; more than 50%; more than 60%; or more than 70% of the nanotubes are free of catalyst nanoparticles used for carbon nanotube formation. In a further embodiment, more that 80%, or yet further, more than 90%, or even further more than 95% of the nanotubes are free of catalyst nanoparticles used for carbon nanotube formation.

The carbon nanotubes in a membrane also can be characterized by an areal density. For example, areal density can be for example at least $1 \times 10^{10}$/square centimeter, or alternatively at least $1.5 \times 10^{10}$/square centimeter, or alternatively at least $2 \times 10^{10}$/square centimeter, or alternatively at least $2.5 \times 10^{10}$/square centimeter, or alternatively, at least $3 \times 10^{10}$/square centimeter, or alternatively at least $3.5 \times 10^{10}$/square centimeter, or alternatively at least $4 \times 10^{10}$/square centimeter.

The carbon nanotubes in a membrane also can also be characterized by a charge density. For example, charge density can be for example at least about 0.5-4 mM, or alternatively at least 1-3 mM, or alternatively at least 2-3 mM, or alternatively at least 1-2 mM, or alternatively, at least 1.5-3 mM, or alternatively at least 0.5-2 mM, or alternatively at least 1.5-2.5 mM.

The carbon nanotubes can be characterized by an average length. The upper end on length is not particularly limited and CNTs hundreds of microns long, such as 500 microns long, can be made. For example, average length can be about 0.1 microns to about 500 microns, or about 5 microns to about 250 microns, or about 0.1 microns to about 5 microns, or about 0.2 microns to about 20 microns, or about 0.2 microns to about 10 microns, or about 0.2 microns to about 5 microns. Average length can be greater than about 0.5 micron, or alternatively greater than about 1 microns, or alternatively, greater than about 3 microns, or alternatively, greater than about 4 microns, or alternatively, about 5 microns to about 100 microns, or alternatively, about 5 microns to about 150 microns, or alternatively, about 5 microns to about 50 microns, or yet further about 1 micron to about 50 microns. The carbon nanotubes arranged in an array can be characterized by high aspect ratio gaps between the individual carbon nanotubes, wherein the length is much greater than the width. For example, aspect ratio of these gaps can be at least 1,000 length/width.

For the pore sizes described herein, efficient ion rejection is largely due to the electrostatic repulsion between the charges strategically placed on the through-pore entrance and the co-ions in solutions. Efficient ion rejection is achieved for millimolar or sub-millimolar salt concentration. Increasing the number of charges at the nanopore entrance by targeted functionalization improves ion rejection performances. For larger pore diameters, rejection performances may degrade quickly with increasing nanotube size. In another embodiment of this invention, the charged carbon nanotube pores have a sub-nanometer diameter. For these carbon nanotube sizes, efficient ion exclusion is obtained for much larger salt solution concentrations due to the simultaneous contribution of steric hindrance, size exclusion, and electrostatic repulsion mechanisms.

Pressure-driven filtration experiments, coupled with capillary electrophoresis analysis of the permeate and feed, are used to quantify ion exclusion in these membranes as a function of solution ionic strength, pH, and ion valence. In some embodiments, the carbon nanotube membranes exhibit ion exclusion as high as 98% under certain conditions. In some embodiments, the ion exclusion results may support a Donnan-type rejection mechanism, dominated by electrostatic interactions between fixed membrane charges and mobile ions, while steric and hydrodynamic effects may be minor or negligible.

A model of nanofluidic platform consisting of sub-2 nm carbon nanotube membranes fabricated by conformal deposition of silicon nitride on densely-packed, vertically-aligned carbon nanotube forests has been demonstrated (FIG. 1a-c) (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312:1034-1037). The etching process is used to expose and to selectively uncap the carbon nanotubes to introduce hydroxyl (OH), carbonyl (C=O), and carboxylic (COOH) functional groups at the nanotube entrance (Yang D Q, Rochette J F, Sacher E (2005) Controlled chemical functionalization of multiwalled carbon nanotubes by kiloelectronvolt argon ion treatment and air exposure. *Langmuir* 21:8539-8545; and Li P H, Lim X D, Zhu Y W, Yu T, Ong C K, Shen Z X, Wee A T S, Sow C H (2007) Tailoring wettability change on aligned and patterned carbon nanotube films for selective assembly. *J Phys Chem B* 111:1672-1678). In particular, ionization of these carboxylic groups provides a ring of negative charges at the pore entrance that could affect the ion transport through the nanotube pore.

3. Membranes

In one aspect, there is provided a membrane for an enhanced fluid transport comprising, consisting essentially of, or consisting of a substantially vertically-aligned array of carbon nanotubes as provided herein and a matrix material disposed between the carbon nanotubes. In a particular embodiment, there is provided a membrane for an enhanced fluid transport comprising, consisting essentially of, or consisting of a substantially vertically-aligned array of carbon nanotubes functionalized at least one end of at least one of the nanotubes, wherein the nanotubes have average pore size of about 6 nm or less and a matrix material disposed between the carbon nanotubes.

In another embodiment, there is provided a membrane for an enhanced transport of desalted water from salted water comprising, consisting essentially of, or consisting of: a substantially vertically-aligned array of carbon nanotubes, wherein the nanotubes have average pore size of about 1-2 nm having at least one functionalized nanotube; and a matrix material disposed between the carbon nanotubes.

In another embodiment, it is contemplated that the membranes may be used to selectively transport certain ions, but reject other ions across the membrane. This may be achieved by selecting a functional group at the end of the nanotube that rejects certain ions while allowing other ions to transport across the membrane.

In yet another embodiment, there is provided a membrane for an enhanced transport of desalted water from salted water comprising, consisting essentially of, or consisting of: a substantially vertically-aligned array of carbon nanotubes, wherein the nanotubes have average pore size of about 1-2 nm with a charge density of about 1-3 mM and have at least one functionalized nanotube; and a matrix material disposed between the carbon nanotubes.

In some embodiments, the membrane described herein provides an enhanced selectivity in the transport of the fluid larger than a non-functionalized nanotube. In some embodiments, the membrane described herein provides an enhanced rejection of the salt from a salted water than a non-functionalized nanotube.

These membranes can have pore sizes on the molecular scale (ranging from approximately 1 nm to approximately 2 nm). They are robust, mechanically and chemically stable. Enhanced gas transport through the membranes compared to other materials of similar pore size is demonstrated. Molecular dynamics simulations predict high water flows through these materials too. Due to high molecular flux and possibility of size exclusion, the possible applications of these materials include but are not limited to: 1) Gas separations such as (but not limited to) removal of hydrocarbons, $CO_2$ sequestration; 2) water desalination/demineralization (described below); 3) dialysis; and 4) breathable material for protection from chemical and biological agents.

The nanoporous membranes can be fabricated from a variety of a substantially vertically aligned array of single wall, double-walled, or multi-wall CNTs, grown via an atmospheric pressure chemical vapor deposition process, as known in the art. For example, ethylene, hydrogen, and argon can be used as process gases, and a thin metal multilayer deposited on silicon can serve as the substrate to catalyze the growth. It is the uniqueness of the metal catalyst layer that enables one to grow carbon nanotubes, including SWCNTs, in a substantially vertically aligned array, as opposed to growth in the plane of the substrate. This vertically aligned array of nanotubes typically has internal diameters ranging from, for example, 0.8-2 nm, a tube-tube spacing of less than 50 nm, preferably 1.0 to 5.0 nm, and a height (thickness) of 5-10 µm. MWCNT arrays may have internal diameters on the order of 5-20 nm.

Once grown, the nanotube array can be coated by a matrix material to immobilize the tubes and enable processing into a membrane. Matrix fill can be continuous or form a closed cell structure. A factor here is the use of a conformal material that can fill the high aspect ratio (approximately 1000 length/diameter) gaps between these tubes, such that the carbon nanotubes serve as the only pores in the material. A variety of matrix materials, ranging from inorganic material to polymeric material (e.g. parylene, polydimethylsiloxane, polyimide) may be used. Polymeric material includes, but is not limited to, linear polymers such as polyethylene, polyacrylates, or polystyrene and cross linked polymers such as epoxy resins. It can also be semi-permeable such as polyamide or non-permeable such as epoxy resin.

Examples of inorganic material include, but are not limited to, ceramics (e.g. silicon nitride, silicon dioxide). The matrix material can also be for example an oxide material such as for example silicon or aluminum oxide. Silicon oxide materials can be made from, for example, (TEOS) tetraethyloxysilane. The matrix material could also include silicon from, for example, a silicon source. Polysilicon can be used.

Any number of additional matrix materials can be used which can have the functional characteristics of having negligible, low or high molecular permeability. In some embodiments, the matric material has a selective molecular permeability where it allows certain molecules to penetrate while preventing others. Other functional characteristics can include optical impermeability, or opaqueness, indicating transmitting negligible light intensity over a certain range of wavelengths, compared to the internal space of the carbon nanotubes. Matrix can also be transparent. The membrane can have a thickness of for example about 100 nm to about 2 microns, or about 400 nm to about 800 nm.

Low-stress silicon nitride and TEOS oxide (tetraethoxysilane oxide) have been successfully used to achieve conformal, void-free coatings on multiwall nanotube arrays (outer diameters of 20-50 nm), resulting in a high strength composite membrane. In addition to using CVD (Chemical Vapor Deposition) coatings, filling can be achieved using Atomic Layer Deposition. In some embodiments, the matrix material comprises a ceramic. In some embodiments, the matrix material comprises silicon nitride. In some embodiments, the matrix material comprises low stress silicon nitride. In some embodiments, the matrix material comprises a polymer. In some embodiments, the matrix material comprises TEOS oxide.

It is to be noted that ceramics like silicon nitride are particularly advantageous for desalting/demineralization applications, due both to their high temperature stability (films deposited at 800° C.) and solvent resistance (to strong acids/bases), which would facilitate removal of the organic and inorganic foulants on the membrane. Parylene has also exhibited conformal properties on multiwall CNT arrays, with both high temperature stability (melting point up to 420° C.) and solvent resistance.

Provided herein is a method for producing a CNT-based membrane using low-stress silicon nitride as a conformal matrix material. This method provides a graphitic CNT membrane using a ceramic matrix material. In contrast to polymer matrices, silicon nitride has a negligible molecular permeability, leaving the cores of embedded CNTs as the only pores in the membrane. In addition, the nanotubes can also serve as a template for the production of nanoporous silicon nitride since they can be selectively removed by oxidation. Another advantage of silicon nitride is its vapor phase deposition. Materials deposited in the liquid phase such as spun-on polymers may involve elaborate curing processes to reduce CNT agglomeration and ensure retention of alignment.

In some embodiments, the matrix material has negligible molecular permeability. In some embodiments, the matrix material is a rigid material. In some embodiments, the membrane has a thickness of about 0.1 microns to about 2 microns. In some embodiments, the matrix material has a thickness of about 400 nm to about 800 nm.

It may be desirable to ensure adhesion between the carbon nanotube and the matrix such that the composite material as a whole is mechanically robust. In some embodiments, the matrix material encapsulates the carbon nanotubes. In some embodiments, the matrix material conformally coats the carbon nanotubes. In some embodiments, the matrix material is free of gaps between the outer surface of the nanotubes and the matrix material. To this end, tensile strain tests on the material, as well as nanoindentation tests to examine closely the nanotube/matrix interface can be carried out. In some embodiments, the membrane does not fracture when tested with a one atmosphere pressure drop.

In one aspect, the membranes are characterized functionally in that they should not pass particles or nanoparticles such as for example 100 nm or 25 nm fluorescently labeled polystyrene beads or metallic nanoparticles of for example size of 2, 5, or 10 nm. In additional, microscopic and spectroscopic techniques using AFM (atomic force microscopy) and UV-VIS spectroscopy can functionally characterize the exclusion of 2 nm gold colloidal nanoparticles in membrane permeation.

In some embodiments, the membrane does not pass 100 nm fluorescently-labeled polystyrene beads. In some embodiments, the membrane does not pass 25 nm fluorescently-labeled polystyrene beads. In some embodiments, the membrane does not pass 2 nm, 5 nm, or 10 nm gold nanoparticles.

In some embodiments, the gaps in the nanotubes are high aspect ratio gaps of about 1,000 length/diameter or less. In some embodiments, the gaps are high aspect ratio gaps of at least about 100 length/diameter.

In some embodiments, the membrane provides enhanced gas transport compared to the Knudsen transport prediction for same sized pores. In some embodiments, the membrane provides enhanced gas transport compared to the Knudsen transport prediction for same sized pores, wherein the enhancement is at least three orders of magnitude for an air flow rate. In some embodiments, the membrane provides enhanced gas transport compared to the Knudsen transport prediction for same sized pores, wherein the enhancement is at least 16 times that for an air flow rate. In some embodiments, the membrane provides enhanced gas transport compared to the Knudsen transport prediction for same sized pores, wherein the enhancement is at least 50 times that for an air flow rate.

In some embodiments, the membrane provides enhancement of water flow over no-slip, hydrodynamic flow prediction. In some embodiments, the membrane provides enhancement of water flow over no-slip, hydrodynamic flow by at least 10 times. In some embodiments, the membrane provides enhancement of water flow over no-slip, hydrodynamic flow by at least 500 times.

In some embodiments, the membrane provides an air permeability of at least one cc/s-cm$^2$-atm and a water permeability of at least one mm$^3$/s-cm$^2$-atm. In some embodiments, the membrane provides an air permeability of at least two cc/s-cm$^2$-atm and a water permeability of at least two mm$^3$/s-cm$^2$-atm. In some embodiments, the membrane provides a gas selectivity relative to helium which is higher than that from a Knudsen model.

In each of the embodiments described herein, it should be understood, although not explicitly stated that the nanotubes have a height of about 0.2 microns to about 5 microns, and the matrix material comprises a ceramic or polymer. In some embodiments, the nanotubes have a height of about 0.2 microns to about 5 microns, and the matrix material comprises a polymer. In some embodiments, the nanotubes have a height of about 0.2 microns to about 5 microns, and the matrix material comprises a ceramic. In some embodiments, the membrane provides enhanced gas transport compared to Knudsen transport prediction for same sized pores.

In some embodiments, there is provided a membrane for an enhanced transport of desalted water from salted water comprising, consisting essentially of, or consisting of a substantially vertically-aligned array of carbon nanotubes, wherein the nanotubes have average pore size of about 1-2 nm having at least one functionalized nanotube; and a matrix material disposed between the carbon nanotubes, wherein the membrane provides an enhanced selectivity in the transport of desalted water from salted water than a nanotube without a functionalized tip.

In some embodiments, there is provided a membrane for an enhanced transport of desalted water from salted water comprising, consisting essentially of, or consisting of: a substantially vertically-aligned array of carbon nanotubes, wherein the nanotubes have average pore size of about 1-2 nm having at least one functionalized nanotube; and a matrix material disposed between the carbon nanotubes, wherein the membrane provides an enhanced rejection of the salt from a salted water than a nanotube without a functionalized tip.

In some embodiments, there is provided a membrane for an enhanced transport of desalted water from salted water comprising, consisting essentially of, or consisting of: a substantially vertically-aligned array of carbon nanotubes, wherein the nanotubes have average pore size of about 1-2 nm with a charge density of about 1-3 mM and have at least one functionalized nanotube; and a matrix material disposed between the carbon nanotubes, wherein the membrane provides an enhanced rejection of the salt from a salted water than a nanotube without a functionalized tip.

After coating, the excess matrix material can be removed from the membrane, and the carbon nanotubes can be opened, as they are initially capped at the top and blocked at the bottom with catalyst particles. This can be easily achieved by use of a plasma etching process.

In some embodiments, there is provided a nanoporous membrane prepared by the methods described herein. In some embodiments, the substantially vertically aligned carbon nanotube array in the nanoporous membrane is a single wall array, and the nanotubes have diameters on the order of 0.8 nm to 2 nm, a tube-tube spacing of less than 50 nm, and a height of 5 microns to 10 microns. In some embodiments, the vertically aligned carbon nanotube array in the nanoporous membrane is a multi wall array, and the nanotubes have diameters on the order of 5 nm to 10 nm, a tube-tube spacing of less than 5 nm, and a height of 5 microns to 10 microns.

Another embodiment is a fabric comprising, consisting essentially of, or consisting of the membrane having the array of nanotubes as provided herein and a porous polymer or fiber fabric supporting material. Articles can include articles that comprise a plurality of membranes including for example chips comprising, consisting essentially of, or consisting of a plurality of membranes, as well as systems and devices wherein membranes are placed on top of each other in multilayer formats.

4. Method of Making Membranes

Fabrications methods for the membranes provided herein, can comprise at least two general steps. In a first step, the array of substantially vertically aligned carbon nanotubes can be fabricated. In a second step, the gaps between the nanotubes can be filled with matrix material. Vapor deposition can be used for either or both steps. The carbon nanotubes can be processed so that they are sufficiently open and provide for fluid flow. In some cases, the filling step can be carried out when the carbon nanotubes are closed, but then the carbon nanotubes can be subsequently opened by for example etching.

If desired, carbon nanotubes can be removed by for example oxidation to leave open channels free of or substantially free of carbon nanotubes. Vapor deposition can be used by methods known in the art and described in the working examples below. The carbon nanotubes can be grown on a substrate comprising metallic nanoparticles or metallic layers. For filling the gaps between the carbon nanotubes, vapor deposition can be used including chemical vapor deposition.

Some embodiments of the membrane structure are as defined in FIG. 10.

In some embodiments, CNTs are substantially aligned and span the whole membrane thickness. An embodiment of such membrane structure is as shown in FIG. 10A. These membranes could be made using CNTs that get aligned on a substrate during CVD synthesis. CNTs are functionalized after being embedded in a matrix.

In some embodiments, CNTs are randomly dispersed in a matrix and the molecular flow partially happens through CNTs and partially through the matrix. An embodiment of such membrane structure is as shown in FIG. 10B. These membranes can be made using unaligned bulk CNTs that are dispersed into a matrix. The functionalization of CNTs is performed before they are embedded into the matrix. The matrix in this case is semi-permeable for molecules, retaining some and letting others go through. The permeability of the matrix alone for the molecules of interest is low. The addition of dispersed CNTs provide high flux channels for molecular transport that enhance the permeability of the membrane at least 2× and up to 100× compared to membranes without CNTs. Functional groups on CNTs serve two purposes for these membranes: 1) they improve membrane selectivity and 2) they enable better dispersion of CNTs in a matrix, allowing for higher CNT density and enhanced permeability.

In some embodiments, the membrane structure is similar to the membrane structure depicted in FIG. 10B except that the CNTs are aligned or partially aligned using an external field such as electric field (as shown in FIG. 10C). The alignment of the CNTs using an electric field is provided in detail below. Alignment further improves permeability by reducing the path length a permeable molecule has to follow to cross the entire membrane thickness.

In some embodiments, the membrane structure is similar to the membrane structure depicted in FIG. 10A except that CNTs are not aligned and the CNTs that span the membrane thickness only contribute to the permeability (as shown in FIG. 10D).

In some embodiments, the membrane structure is similar to the membrane structure depicted in FIG. 10A and further where the matrix acts as a semi-permeable material and the functionalized aligned CNTs contribute also to the permeability and selectivity of the membrane.

In some embodiments, the membrane structure is similar to the membrane structure depicted in FIG. 10D and further where the matrix acts as a semi-permeable material and the randomly dispersed, functionalized CNTs (both embedded and spanning the whole membrane thickness) contribute also to the permeability and selectivity of the membrane.

Figure 11A:
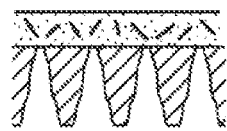
FIG. 11 illustrates various embodiments of the membrane structure on a backing.
Figure 11B:
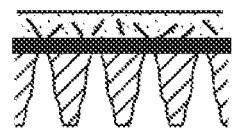

The membrane structures, as described herein, can be supported on a backing material. As shown in FIG. 11, the membrane structure can be directly on a backing (FIG. 11A), on a backing with a cushion layer (such as hydrogel, FIG. 11B) or free standing, supported on a mesh. For example, the membranes on a backing could be synthesized using interfacial polymerization with CNTs added into either organic or aqueous phase.

Figure 12:
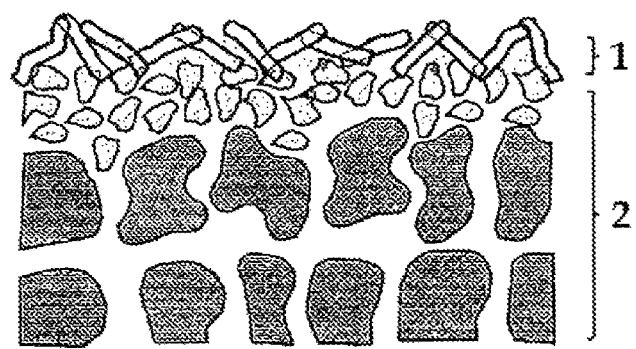
FIG. 12 illustrates another embodiment of the membrane structure of the invention.

In yet another embodiment, the CNTs are dispersed in such a way that the CNTs are longer than the thickness of the film. An example of such embodiment is as shown in FIG. 12. In this embodiment, bulk CNTs are added to the polymer before membrane fabrication. As the result of the process, CNTs are randomly oriented in the membrane, which causes a significant portion of the nanotubes to span the whole membrane thickness. Membrane etching on both sides then produces a permeable membrane. In some embodiments, the top surface of the CNT array is coated with a protective layer (skin layer), such as fast depositing parylene (PA) that prevents the CNTs from collapsing into each other during matrix infiltration. This selective skin layer is shown as 1 in FIG. 12. In some embodiments, the membrane structure comprises a porous bottom support structure, shown as 2 in FIG. 12, which acts as a boundary confining surface. Examples of bottom support structure include, but are not limited to, polysulfone (PSF), polyethersulfone (PES), etc. The membrane may be opened by either etching the whole protective parylene layer or just opening the CNT pores on top of the parylene layer. In some embodiments, the transport of the fluid can also go through the fill.

In one aspect, the fabrication sequence of the membrane structure of FIG. 12 comprises, consists essentially of or consists of the following steps:
a) Functionalized CNTs are dispersed in an aqueous phase (for example, water, m-phenylenediamine etc.) or solvent phase (for example, hexane, trimesoylchloride, etc.);
b) PSF membrane support is dipped into the aqueous phase;
c) excess aqueous solution is removed from the surface of the membrane support;
d) the membrane support is dipped into the solvent phase;
e) the membrane support is cured at the oven; and
f) stored in water.

Figure 13:
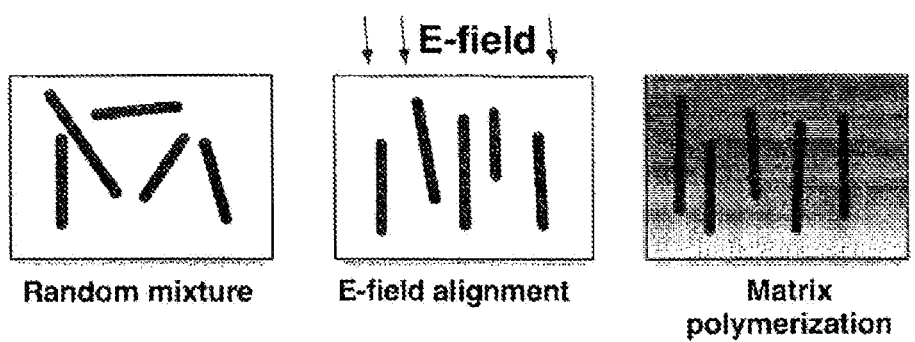
FIG. 13 illustrates a membrane structure where the CNTs are aligned by using an electric field.

In some aspects, an electric field is used to align the CNTs for membrane fabrication. An example of such embodiment, is as shown in FIG. 13. This procedure uses the conducting nature of CNTs or a fraction of CNTs. The application of electric field (either a DC or AC field) results in the induced torque on the CNTs that orients them parallel to the E-field lines. Thus at least a large portion of the CNTs in the matrix becomes oriented. Then the matrix is cured to permanently immobilize the CNTs in the aligned orientation. The curing methods include, but are not limited to, heat, radical polymerization, UV cure or the like.

In some embodiments, the fabrication sequence of the membrane structure using an electric field comprises, consists essentially of or consists of the following steps:

a) chemically-modified SWNTs (for example, amine) are dispersed in a solvent (for example, THF);
b) the dispersed SWNT solution is mixed with a polymer (for example, epoxy);
c) the mixture is magnetically stirred;
d) Indium Tin Oxide (ITO) glass coated with thin polyvinyl acetate (PVA) layer is prepared (that allows for release of the structure in water);
e) the SWNT/polymer solution is dropped between ITO glasses;
f) AC electric field is applied; and
g) after curing or evaporation of the solvent, the assembly is put into water bath to remove PVA layer and separate SWNT/polymer film from ITO glass.

Figure 18:
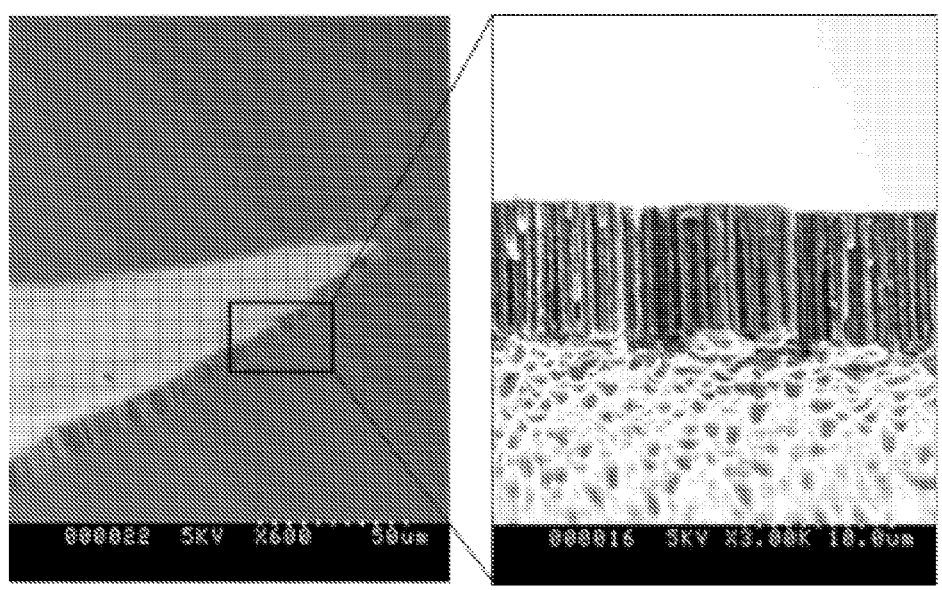
FIG. 18 illustrates a membrane structure where a carbon nanotube array is filled with a parylene polymer by vapor phase infiltration.

In yet another embodiment, there is provided a membrane structure and a fabricaton sequence of the membrane structure using a vapor phase infiltration of carbon nanotube array with parylene polymer fill. An example of such embodiment is illustrated in FIG. 18. In this embodiment, the nanotube array is coated by polymeric material deposited from vapor phase (for example, parylene) to fill the space between the nanotubes to create a matrix that holds the nanotubes together and precludes mass transport through that filled layer through any other channels except the inner pores of carbon nanotubes. The filled CNT layer can then be released from the substrate to form a free-standing membrane that can then be etched from both sides to form a permeable membrane.

Other embodiments for making the membranes are described below. Without limited by any theory, it is to be understood that the order of one or more steps may be altered in the methods of making the membrane described herein.

In one aspect, there is provided a method of making a membrane comprising, consisting essentially of, or consisting of:
a) fabricating a substantially vertically-aligned array of carbon nanotubes wherein the nanotubes have average pore size of about 2 nm or less, and wherein the array comprises gaps between the carbon nanotubes;
b) filling the gaps between the nanotubes with a ceramic matrix material;
c) opening the nanotubes providing flow through the membrane; and
d) functionalizing a tip of the nanotube with a functional group.

In another aspect, there is provided a method of making a membrane for enhanced fluid transport comprising, consisting essentially of, or consisting of:
a) providing a substantially vertically-aligned array of carbon nanotubes wherein the nanotubes have average pore size of about 2 nm or less;
b) disposing a matrix material between the carbon nanotubes;
c) opening the nanotubes providing flow through the membrane; and
d) functionalizing a tip of the nanotube with a functional group.

In another aspect, there is provided a method for fabricating nanoporous membranes comprising, consisting essentially of, or consisting of:
a) growing a substantially vertically aligned carbon nanotube array on a substrate with high aspect ratio gaps between the nanotubes wherein the nanotubes have average pore size of about 2 nm or less;
b) coating the array with a conformal matrix material capable of conformably filling the high aspect ratio gaps between the nanotubes to immobilize the nanotubes upon hardening of the conformal matrix material;

c) opening the ends of the nanotubes; and
d) functionalizing a tip of the nanotube with a functional group.

In yet another aspect, there is provided a method of making a membrane comprising, consisting essentially of, or consisting of:
a) fabricating a substantially vertically-aligned array of carbon nanotubes, wherein the nanotubes have average pore size of about 2 nm or less and wherein the array comprises gaps between the carbon nanotubes;
b) filling the gaps between the nanotubes with polymeric matrix material;
c) opening the nanotubes providing flow through the membrane; and
d) functionalizing a tip of the nanotube with a functional group.

In some embodiments, the fabrication step comprises vapor deposition. In some embodiments, the filling step comprises vapor deposition. In some embodiments, the fabrication step comprises vapor deposition, and the filling step comprises vapor deposition.

In some embodiments, the fabrication step comprises providing a substrate surface comprising, consisting essentially of, or consisting of metal nanoparticle catalyst for vapor deposition. In some embodiments, a thin metal multilayer deposited on silicon is used as the substrate to catalyze the growth. In some embodiments, the thin metal multilayer is Fe. In some embodiments, the thin metal multilayer has a thickness of about 5 nm to about 10 nm.

In some embodiments, the filling step comprises chemical vapor deposition. In some embodiments, the filling step comprises vapor deposition when the carbon nanotubes are capped.

In some embodiments, the methods further comprise etching on both sides of the membrane to open the carbon nanotubes. In some embodiments, the methods further comprise removing the carbon nanotubes.

In some embodiments, the methods further comprise removing the nanotubes after hardening of the matrix material. In some embodiments, the nanotubes are removed by oxidation.

In some embodiments, acetylene, ethylene, hydrogen, and argon are used as process gases for growing the nanotube array. Without limited by any theory, it is to be understood that any carbon containing gas may be used in this process.

In some embodiments, the conformal material is silicon nitride. In some embodiments, the conformal material is TEOS oxide.

In some embodiments, the CVD is used for the coating process. In some embodiments, the ALD is used for the coating process.

In some embodiments, the nanotubes are opened by removing excess matrix material from the membrane. In some embodiments, the excess matrix material is removed from the membrane using a plasma etching process.

In some embodiments, the polymeric matrix material comprises parylene.

4. Method of Using Membranes

A further embodiment is a method for separating analytes from a fluid and therefore purifying a fluid by passing the liquid or gas to be purified through at least one carbon nanotube as described herein. In one aspect, the nanotubes are contained within a membrane and the fluid to be purified is water for example from fresh water sources or sea water containing salt. In some embodiments, the liquid is blood or plasma. The method may also comprise collecting the liquid or gas after passing through the one or more nanotubes.

Water Desalination

Further described herein are water flow measurements through microfabricated membranes with sub-6 nanometer (inner diameter) aligned functionalized carbon nanotubes as pores. The measured water flow exceeds values calculated from continuum hydrodynamics models by more than two orders of magnitude and is comparable to flow rates extrapolated from molecular dynamics simulations. The gas and water permeabilities of these nanotube-based membranes are several orders of magnitude higher than those of commercial polycarbonate membranes, despite having order of magnitude smaller pore sizes.

The membranes can be used in a wide variety of applications including for example water desalination, water demineralization, gas separation including removal of hydrocarbons, carbon dioxide sequestration, dialysis, and breathable material for protection from chemical and biological agents.

Both charge and size effects can impact exclusion. The nanotubes are charged at the end with positive or negative charges so that charged particles can be repulsed or attracted to the nanotubes. Charge prevents ions from entering the nanotube which might otherwise enter the nanotube if not for the charge.

Membranes can be used on substrates including for example silicon or glass substrates, as well as porous substrates. Another application is for use as a high capacity adsorbent material.

The membranes provided herein can be used in various fluid or liquid separation methods, e.g., water purification, demineralization, and desalination. For a general review of desalination procedures see "Review of the Desalination and Water Purification Technology Roadmap" available from the United States Bureau of Reclamation, United States Department of the Interior. See also for example U.S. Pat. Nos. 4,302,336; 4,434,057; 5,102,550, 5,051,178, and 5,376,253.

The CNT membranes can operate on the basis of both size and charge screening (Donnan exclusion and Coulombic repulsion) effects. Although many conventional membranes rely on both effects, a novelty point for this CNT membrane lies in the higher water flux achievable under conventional operating pressures. While the present embodiments are not limited by theory, some principles are noted. The nanometer size of CNTs (for example, 0.5-6 nm), which approaches that of many solvated ions of interest to desalination process, suggests that many species would be unable to enter the nanotube and make it across the membrane. Indeed, recent molecular dynamics simulations of osmotic water transport through carbon nanotube membranes (Karla et al. (2004) *PNAS* 100(18):10175) suggest that 0.8 nm diameter carbon nanotubes are sufficient to block species as small as hydrated $Na^+$ and $Cl^-$. Yet another screening effect is caused by charge layer overlap at the "mouth" of the nanotube pore where charges are present (Miller et al. (2001) *JACS* 13(49):12335).

In electrolyte solutions, counterions present (those of opposite charge to the functional groups on the membrane surface) to balance these tip charges. Under the appropriate ionic strength and pore size, an overlap of these counterion charge layers occurs. The net effect of this is the creation of an "ion gate" that will exclude co-ions of like charge with the functional groups and only permit counterions to pass through the channel. As a result, the CNT membrane is designed for cation (for acid functionality) or anion (for base functionality) transmission. A characteristic of this type of exclusion is a dependency on the co-ion valency. For example, for a base-functionalized membrane (carrying positive charge), species such as $Ca^{2+}$ and $Mg^{2+}$ would be rejected to a greater extent than monovalent species like $Na^+$ and $K^+$ (Yaroshchuk, A. (2001) *Sep. and Purification Tech.* 143:22-23).

High water permeability for the proposed membrane can be carried out and the results interpreted in view of several studies (for example, Kahn et al. (2004) *PNAS* 100(18):10175; Hummer, G. (2001) *Nature* 414:188; Koga, et al. (2001) *Nature* 412:802) that have predicted high water flux through SWCNTs. The high flux predictions are partly a consequence of inherent atomic nanotube interior, which leads to nearly frictionless transport. Another factor, which appears to be unique to the non-polar CNT/polar molecule system, relates to molecular ordering that can occur on this nanometer scale. These molecular dynamic simulations (Kahn et al. (2004) *PNAS* 100(18):10175; Hummer, G. (2001) *Nature* 414:188; Koga, et al. (2001) *Nature* 412:802) have suggested one-dimensional ordering of water molecules confined within carbon nanotubes, leading to single hydrogen bonds between them. These so-called "water wires", which are of relevance in biological systems (Rouseau, et al. (2004) *Phys. Chem. Chem Phys.* 6:1848), are able to shuttle in and out of the carbon nanotube channels rapidly as a consequence of their ordering and non-interaction with the pore walls. Recent experiments using neutron diffraction have indeed confirmed the existence of these "water wires" within carbon nanotube pores (Kolesnikov, A. (2004) *Phys. Rev. Lett.* 93: 035503-1), suggesting that the predicted rapid transport rates should be experimentally observable.

Water desalination can be carried out by passing the water through multiple membranes to produce purification which removes for example at least 50 mole percent, or at least 60 mole percent, or at least 70 mole percent, or at least 80 mole percent, or at least 90 mole percent of the target molecule or ion such as for example chloride or sodium.

Fabric

This section describes the development of a chemical/biological (CB) agent-resistant membrane based upon carbon nanotube including single wall carbon nanotube membranes, as described herein. This membrane can act as a molecular sieve, exhibiting size selectivity against large molecules, a category into which many CB agents may fall (e.g., VX, Sarin, Mustard). The size selectivity of the nanotubes enables air and moisture to be exchanged, while acting as a barrier against CB agents. This combination creates a "breathable material" that can be eventually incorporated into a CB garment, suitable for use, by a warfighter.

A robust membrane comprising substantially vertically-aligned CNTs, or randomly oriented nanotubes, embedded in a biocompatible, gas- and liquid-impermeable polymer matrix material can be fabricated. The nanotubes can span the membrane and will be open on both sides, serving as the only channel for air and water permeation. As a consequence of the uniqueness of the carbon nanotube surface, high air and water permeability can be achieved, making this membrane a choice for incorporation into a garment. The CNT membrane can satisfy the needs of the warfighter, while offering superior performance to conventional materials used. Without being bound by theory, the size exclusion basis of operation of this CNT membrane is believed to provide its greatest advantage over conventional activated carbon, adsorption-based materials, as well as over membrane-based fabric that feature larger pore sizes. Significantly, comparable or better air permeability can be achieved, despite the much smaller pore size. This membrane is also flexible, durable, and resistant to fouling.

One of the issues with the current protective fabrics is their inability to provide high breathability and high degree of protection at the same time. Some of the current robust protective fabrics (e.g. solid membrane chemical protective suits) have substandard breathability and some of the more breathable fabrics (LANX) provide substandard or temporary protection. Fabrics incorporating CNT membranes of the invention combine high protective capability (enabled by chemical modification of CNT pores to provide selectivity) with high breathability provided by unique transport efficiency of CNT pores. This combination distinguishes CNT membrane-based fabrics from other types of protective fabrics.

Protective fabrics are typically incorporated in a "layering" system that comprises an inner layer, a mid layer (optional), and shell layer. Each layer performs a different function: the inner layer, which is closest to the skin absorb sweat and deliver the moisture to the outer layers typically through capillary action, or wicking. The mid-layer provides thermal insulation; therefore it is omitted in warm or moderate climates. The outermost layer, called a shell layer, functions as a protecting layer. It can also provide a good moisture outlet (hence such fabrics are called "breathable" fabrics). Solid polymer garments (such as commonly used chemically-protective butyl rubber gloves) provide good protection to the wearer; yet they cannot transport moisture out, which blocks the main evaporative cooling pathways and creates a humid environment inside the garment. Such environment compromises the individual's health and safety by increasing the risk of heat stress, especially in a moderately warm climate.

An example of the current state-of-the-art shell fabric that provides some level of protection as well as some degree of moisture management is Gore-Tex™, which has become a virtual standard in technical outdoor fabrics. In outdoor use, Gore-Tex™ blocks liquid water and wind, but lets through water vapor (evaporated sweat). A Gore-Tex™ fabric is mainly composed of five layers: (1) abrasion resistant outermost shell, (2) protective mesh, (3) Gore-Tex membrane, (4) protective mesh, and (5) soft inner layer. The Gore-Tex membrane itself is made of thermo-mechanically expanded PTFE (polytetrafluoroethylene) and other fluoropolymers. The typical membrane pore density is ca. $1.4 \times 10^9$ $cm^{-2}$. Estimations bracket the pore size of the membrane between 50 and 150 nm, which is still roughly 700 times larger than the size of a water molecule. The tough exterior layers of the Gore-Tex fabric give the material resistance to mechanical stresses such as abrasion, as well as bear additional water repellant coatings. Liquid water drops may or may not pass through this exterior layer, but if they do, they are stopped by the sub-micron scale hydrophobic fluoropolymer membrane pores. Yet, moisture vapor generated by the skin and passed through the inner layers can still move out through the pores.

Gore-Tex membrane provides a leap in moisture management in comparison with the solid plastic garments, yet its pore size is too large to provide sufficient protection from most CB agents and it fails to satisfy the moisture management requirements in warm climates. In particular, its vapor permeability is still too low to sustain efficient moisture transport driven by a small partial vapor pressure gradients typical for military use in warm climates.

Figure 14:
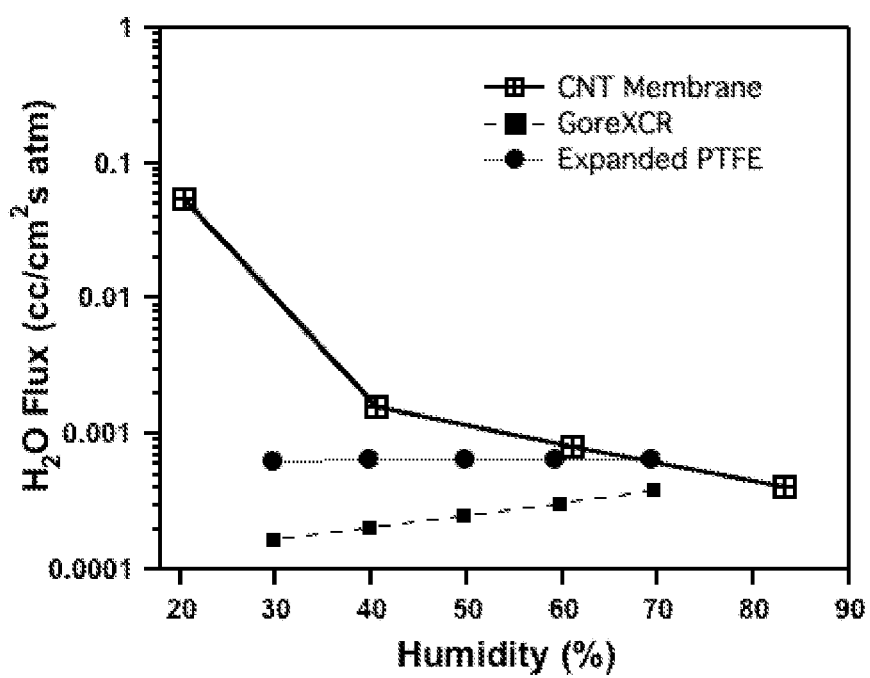
FIG. 14 illustrates a comparison of water vapor fluxes measured for a carbon nanotube membrane and for two commercial PTFE-based membranes that are used in waterproof-breathable fabrics.

Functionalized carbon nanotube membrane of the invention provides two advantages over the existing articles of breathable protective membrane fabrics. First, the CNT pore size are at least 2 orders of magnitude smaller, enabling the membrane to reject large agents based on size exclusion, which could be further enhanced by chemical modification of the pore narrowing it down even more. Second, CNT membrane structure and unique pore characteristics provide enhanced air permeability. CNT membrane has smaller pores but the pore density of those pores is relatively high, typically about $10^{10}$ cm$^{-2}$. Each of those pores has enhanced transport characteristics unique to CNTs. The resulting high air and water vapor permeability of the CNT membrane makes it more breathable than the existing articles of breathable membrane-based fabrics (FIG. 14). FIG. 14 illustrates a comparison of water vapor fluxes measured for a carbon nanotube membrane and for two commercial PTFE-based membranes that are used in waterproof-breathable fabrics. CNT membrane data were collected using a home-built pressure-driven flow test.

Figure 15:
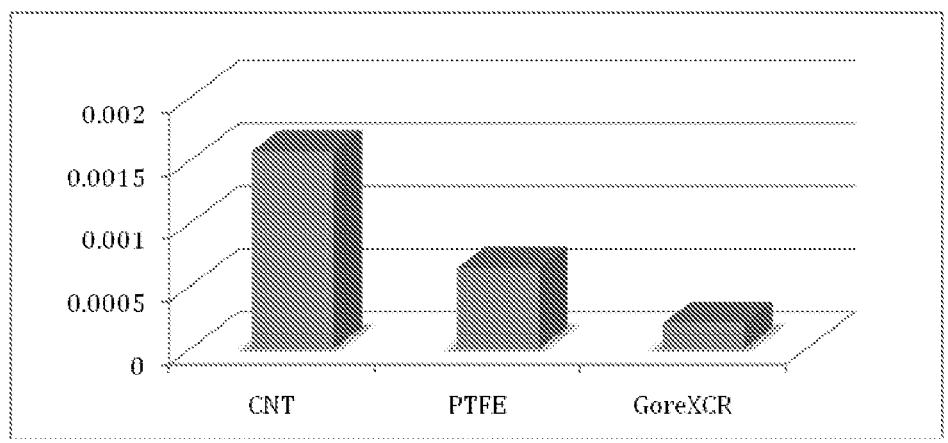
FIG. 15 illustrates breathability of CNT membrane compared with GoreTex™ and PTFE membrane at 40% relative humidity.

In particular, at 40% relative humidity, the water vapor permeability of the CNT membrane was found to exceed the permeability of GoreTex by about an order of magnitude (FIG. 15).

WO 2007/025104, filed Aug. 23, 2006, that describes the nanoporous membranes used for desalination, dialysis and fabric formation, is incorporated herein by reference in its entirety in the present disclosure.

Dialysis

The membranes as described herein also find use in biological applications, e.g., for nanofiltration similar to that performed by the kidney. For example, the nanotubes and membrane containing the nanotubes can be used for separation of analytes in blood or serum and therefore provides methods and materials for dialysis ex vivo and in vivo.

Some of the recent advances in dialysis have been in the area of porosity-controlled, high-flux synthetic membranes. Porosity control is important to achieve the desired separation/sieving profile, with maximal permeability for solutes of <40 kD molecular weight and minimal or no permeation of albumin (48 kD molecular weight, approximately 6-7 nm effective diameter). High-flux membranes offer the important advantage of reducing the treatment time. Multiwall carbon nanotube membranes offer both the requisite porosity control (filtering out albumin on the basis of size exclusion), as well as a much higher flux than that offered by current nanoengineered dialysis membranes. The presence of negatively charged functional groups on the membrane also help reduce the permeation of the similarly charged albumin.

Gas Separation

Figure 5:
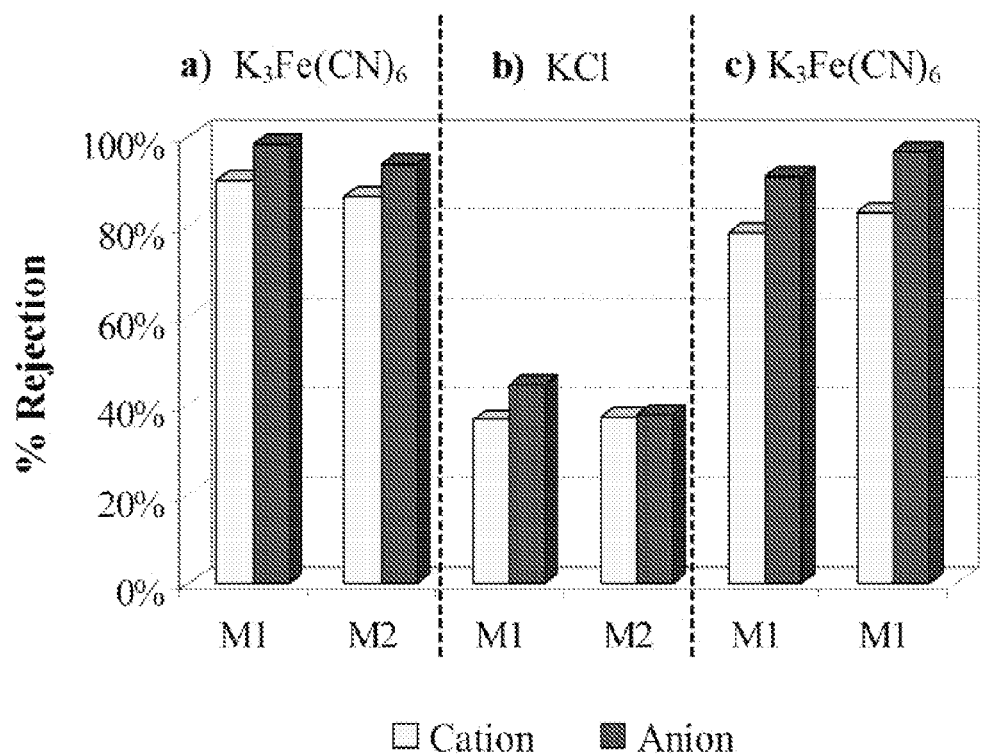
FIG. 5 illustrates comparison of anion and cation rejection coefficients for: (a) two different membranes, M1 and M2, in contact with a 0.3 mM $K_3Fe(CN)_6$ solution, (b) with 1.0 mM KCl solution, and (c) for the same membrane M1 in contact with a 1.0 mM $K_3Fe(CN)_6$ solution.

Gas permeability of MWCNT/SiNx membranes is characterized and membranes show measured rates of up to three orders of magnitude greater than predicted by conventional models. For gas diffusion within the molecular flow regime, wherein the local gas mean free path is more than one order of magnitude greater than the pore diameter, the Knudsen diffusion model is typically applied. This model assumes no interaction between gas molecules and diffuse scattering of gas molecules from the surface dominating. The gas permeability measured for this membrane is up to three orders of magnitude greater than predicted by Knudsen diffusion (shown in WO 2007/025104), assuming the nitrogen porosimetry-observed average pore size of 7 nm and an upper limit of pore density equal to that of the MWCNTs (as observed by scanning electron microscopy). FIG. 5 of WO 2007/025104 presents this data for variety of gases in the form of molecular weight-normalized flow rate versus pressure drop, along with the Knudsen prediction. These results constitute the first experimental demonstration of enhanced gas flux through a carbon nanotube membrane.

Gas permeability of DWCNT/SiNx membranes is characterized and membranes show measured rates of up to two orders of magnitude greater than predicted by conventional models i.e. Knudsen model (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312:1034-1037).

This enhancement in gas flux through carbon nanotubes has previously been predicted by molecular dynamics simulations for SWCNTs, related to their inherent atomic smoothness, leading to spectacular rather than diffuse reflection of gas molecules from the pore surface. In particular, single wall carbon nanotubes are predicted by these simulations to exhibit a three order of magnitude higher gas flux than comparably-sized nanomaterials such as zeolites (nanoporous alumina or silica materials); this flux is also three orders of magnitude lighter than predicted by assuming Knudsen diffusion. More recently, simulations on SWCNTs of up to 8.1 nm in diameter (S. K. Bhatia, H. Chen, and D. S. Sholl, "Comparisons of Diffusive and Viscous Contributions to Transport Coefficients of Light Gases In Single-Walled Carbon Nanotubes", submitted to Molecular Simulation, 2005) have similarly predicted an almost two order of magnitude enhancement as compared with the diffuse reflection limit.

As will be apparent to those of skill in the art, the membranes as described herein can also be for filtration and separation of large airborne particles from gases using the techniques described. Different gases in gas mixtures can also be separated from each other using these membranes. For example, one of the important gas pairs for separation is $CO_2/N_2$. It has been demonstrated that the unfunctionalized membranes do not exhibit high selectivity of $CO_2/N_2$ but that functionalization with groups, such as but not limited to, amine increases the gas selectivity of the membranes. Functionalization often also decreases the permeability of the membrane. Due to the extremely high permeability of sub 6-nm CNT membranes, even with the expected permeability loss of two orders of magnitude due to functionalization, the membranes are still superior to conventional materials (such as mesoporous silica).

Figure 16:
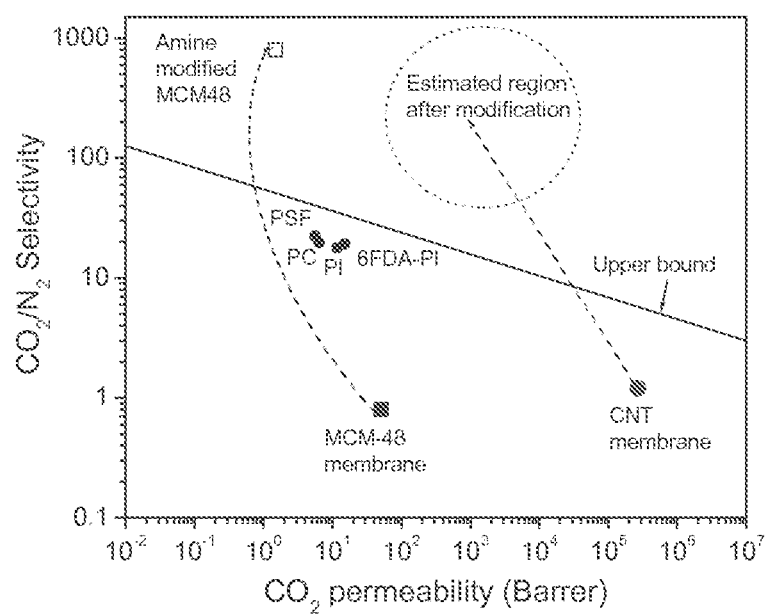
FIG. 16 illustrates comparison of silica membrane with CNT membrane in terms selectivity and permeance.

FIG. 16 illustrates trade-off between the increased selectivity and permeance. For example, functionalized silica membrane showed higher selectivity but the permeance decreased by one or two orders of magnitude (Y. Sakamoto, K. Nagata, K. Yogo and K. Yamada. *Microporous and Mesoporous Materials* 2007, 101, 303-311, P. Kumar, S. Kim, J. Ida, and V. V. Guliants. *Ind. Eng. Chem. Res* 2008, 47, 201-208). With the expected permeance decrease by, at most, two orders of magnitude and high gas selectivities due to functionalization, CNT membrane permeance range is comparable to current mesoporous membrane systems with low gas selectivities. In FIG. 16, MCM48 is mesoporous mobil crystalline materials (MCM)-48 silica membrane; PC is polycarbonate membrane; PI is polyimide membrane; and FDA-PI is 4,4-(hexafluoroisopropylidene)diphthalic anhydride-polyimide or fluorine polyimide membrane.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings

| | |
|---|---|
| AFM = | atomic force microscopy |
| CNT = | carbon nanotube |
| CVD = | chemical vapor deposition |
| DWNT = | double-wall nanotube |
| ITO = | indium tin oxide |
| MD = | molecular dynamics |
| MWNT = | multi-wall nanotube |
| PVA = | polyvinyl acetate |
| RO = | reverse osmosis |
| SWNT = | single-wall nanotube |
| TEM = | transmission electron microscopy |
| TEOS = | tetraethyloxy silane |
| UV-VIS = | ultraviolet-visible |

Example 1

In this study, nanofiltration experiments are used to quantify ion exclusion in the sub-2-nm carbon nanotube pores and to investigate the fundamental mechanisms governing ion transport and ion exclusion in this system. Charged nanochannels can utilize both steric hindrance and electrostatic repulsion to achieve ion rejection (Schaep J, Van der Bruggen B, Vandecasteele C, Wilms D (1998) Influence of ion size and charge in nanofiltration. *Sep Purif Technol* 14:155-162; Schaep J, Vandecasteele C, Mohammad A W, Bowen W R (2001) Modelling the retention of ionic components for different nanofiltration membranes. *Sep Purif Technol* 22-3:169-179; and Childress A E, Elimelech M (2000) Relating nanofiltration membrane performance to membrane charge (electrokinetic) characteristics. *Environ Sci Technol* 34:3710-3716). To understand the relative importance of these rejection mechanisms, ion exclusion and selectivity as a function of solution concentration, pH, ion valence, and ion size is investigated. The measurements obtained in this experiment provide an indication that ion rejection in nanopores of this size is predominantly governed by the electrostatic effects and demonstrate that Donnan's membrane equilibrium model (Donnan FG (1924) The theory of membrane equilibria. *Chem Rev* 1:73-90; and Donnan F G (1995) Theory of membrane equilibria and membrane-potentials in the presence of non-dyalizing electrolytes—A contribution to physical-chemical physiology (reprinted from Zeitshrift fur Elektrochemie and Angewandte Physikalische Chemie, vol 17, pg 572, 1911). *J Membrane Sci* 100:45-55) accounts for most of the experimentally observed transport selectivities.

Materials and Methods

Materials

The salts used in this study are: potassium ferricyanide ($K_3Fe(CN)_6$, 99+% purity, Aldrich, St. Louis, Mo.), potassium chloride (KCl, 99.999%, Aldrich), potassium sulfate ($K_2SO_4$, 99%, Sigma, St. Louis, Mo.), calcium sulfate dehydrate ($CaSO_4$, 98%, Sigma), calcium chloride ($CaCl_2$, 99.5%, EM Science; Darmstadt, Germany), tris(2,2'-bipyridyl) dichlororuthenium hexahydrate ($Ru(bipy)_3Cl_2$, Fluka, Buchs, Switzerland), 1,3,6,8-pyrenetetrasulfonic acid tetrasodium salt ($PTSNa_4$, Invitrogen, Carlsbad, Calif.). 4-methylbenzylamine (97% purity) and α-hydroxyisobutyric acid (α-HIBA) are purchased from Sigma-Aldrich. All salt solutions and buffers are prepared using 18 MΩ water generated by a Milli-Q laboratory water purification system (Millipore, Bedford, Mass.), and subsequently filtered through a 0.1 μm PVDF filter (Millipore).

Membrane Fabrication

Silicon nitride/CNT composite membranes were fabricated according to the previously reported method (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312: 1034-1037). Briefly, a dense, vertically-aligned array of double-walled carbon nanotubes (DWNT) with sub-2 nm diameters is grown by catalytic chemical vapor deposition (CVD) on the surface of a silicon chip using ethylene as carbon source and Fe/Mo as catalyst. Conformal encapsulation of the nanotubes by low-pressure silicon nitride deposition produces a gap-free matrix that fills the volume between DWNTs. Excess silicon nitride on both sides of the membrane and the catalyst particles are removed by argon ion milling. Reactive ion etching in an oxygen containing plasma further exposes and opens the carbon nanotubes. The final result is a silicon nitride membrane with DWNT pores that span the entire membrane thickness and have carboxylic functional groups at their tips (Yang D Q, Rochette J F, Sacher E (2005) Controlled chemical functionalization of multiwalled carbon nanotubes by kiloelectronvolt argon ion treatment and air exposure. *Langmuir* 21:8539-8545; and Li P H, Lim X D, Zhu Y W, Yu T, Ong C K, Shen Z X, Wee A T S, Sow C H (2007) Tailoring wettability change on aligned and patterned carbon nanotube films for selective assembly. *J Phys Chem B* 111:1672-1678). The free-standing membrane area is about 0.175 $mm^2$ with a DWNT density of about 2.5-$10^{11}$ $cm^2$ (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312:1034-1037).

Nanofiltration Experiments

A schematic of the filtration cell is shown in FIG. 1e. A 2×2-cm CNT membrane sandwiched between two O-rings divides the cell in two chambers. The top chamber (feed) is filled with about 2 ml of salt solution, while the bottom chamber (permeate) is sealed with a small vial containing 1 ml of distilled water, whose function is to minimize errors in the measured rejection by limiting permeate evaporation before the analysis of ion concentration. The feed solution is pressurized at 0.69 bar with a controlled nitrogen gas line, while the permeate is at atmospheric pressure. Permeate flow rate is measured as height variation of the column of salt solution in the top chamber with respect to time. When 100-150 μl of solution has permeated through the CNT membrane, the nanofiltration experiment is stopped, and solution samples from both feed and permeate are collected for subsequent analysis by either capillary electrophoresis or UV-vis spectroscopy. Samples that are not immediately analyzed are stored at 4° C. in sealed vials to prevent evaporation. For testing Donnan prediction about the rejection dependence on ion valence, salt solutions with the same equivalent concentration are used: salt content is 0.5 mM for all solutions except KCl (1.0 mM) and $K_3Fe(CN)_6$ (0.3 mM).

Capillary Electrophoresis Analysis

A Hewlett Packard 3D CE capillary electrophoresis system (Agilent Technologies, Santa Clara, Calif.) is used to determine both anion and cation concentration. Fused silica capillaries with 50 μm internal diameter and 40 cm length from injection point to detection window were purchased from Agilent Technologies. Samples are introduced into the capillary by a 5-s hydrodynamic injection at 50 mbar. Non-absorbing ions are detected by indirect UV method. For anion analysis, the running buffer is Agilent inorganic anion buffer (pH=7.7) containing 1,2,4,5-benzenetetracarboxylic acid as background electrolyte; the applied voltage is −25 kV; and the detection wavelength is 210 nm. For cation analysis, either IonPhor cation DDP buffer (pH=4.5) (Dionex, Sunnyvale, Calif.) or UV Cat-1 buffer (Weston A, Brown P R, Heckenberg A L, Jandik P, Jones W R (1992) Effect of electrolyte-composition on the separation of inorganic metal-cations by capillary ion electrophoresis. *J Chromatogr* 602:249-256; and Weston A, Brown P R, Jandik P, Jones W R, Heckenberg A L (1992) Factors affecting the separation of inorganic metal-cations by capillary electrophoresis. *J Chromatogr* 593:289-295) are used as prepared in the laboratory (5 mM 4-methylbenzylamine, 6.5 mM α-hydroxyisobutyric acid; pH=4.3). The detection wavelengths are 225 and 214 nm for IonPhor and UV Cat-1 buffers, respectively, and the applied voltage is 30 kV. A direct detection method is used to measure Ru(bipy)$_3^{2+}$ concentration, since the cation strongly absorbs at 286 and 452 nm. Measurements for feed and permeate concentration (from peak area) are repeated at least three times, and typically agree within 2-3%. Average values are used for rejection calculations.

Experiments Testing Rejection Sensitivity to Solution pH

PTSNa$_4$ rejection is measured at two different pHs, 7.2 (no pH adjustment) and 3.8. A few drops of 0.1N HCl are used to reduce the pH of a 0.5 mM PTSNa$_4$ solution at the desired level while maintaining nearly constant ionic strength and osmotic pressure. The ionic strength, Debye length, and osmotic pressure are 5.0 mM, 4.34 nm, 0.062 bar for the experiment at neutral pH, and 5.16 mM, 4.28 nm, 0.070 bar, respectively, for the experiment at acidic pH. Thus, the added hydrochloric acid for pH adjustment has minor impact on ionic strength, osmotic pressure, and Debye length.

Full PTS$^{4-}$ UV-spectrum is obtained with a Lambda 25 UV-vis spectrometer (PerkinElmer, Waltham, Mass.) after a 1:20 dilution with 18 MΩ water. PTS$^{4-}$ concentration is measured at 244, 283, and 375 nm. Measured anion rejection coefficients are independent of the chosen wavelength. Na$^+$ concentration is obtained by capillary electrophoresis as explained above.

Results

To quantify ion rejection in CNT membranes, pressure driven filtration is used for electrolyte solutions (FIG. 1*e*) followed by capillary electrophoresis (CE) analysis of the ion concentration in the permeate and feed solutions (FIG. 1*f*). Several observations emerge from these experiments. First, carbon nanotube membranes maintain the extraordinarily high rates of water flow reported in the previous study (FIG. 1*d*) (Holt J K, Park H G, Wang Y M, Stadermann M, Artyukhin A B, Grigotopoulos C P, Noy A, Bakajin O (2006) Fast mass transport through sub-2-nanometer carbon nanotubes. *Science* 312:1034-1037). Filtering the ionic solutions through the membrane for extended periods of time does not result in the membrane clogging. Second, CE measurements indicate that CNT membranes reproducibly (see Supporting Information below) exclude a large portion of the ionic species present in the feed solution. For example, passing of 1.0 mM potassium ferricyanide (K$_3$FeCN$_6$) solution under a 0.69 bar pressure differential across the membrane results in the exclusion of ~91% of the anions and 79% of the cations. For 1.0 mM Potassium chloride (KCl) solution under 0.69 bar, CNT membranes exhibit smaller, yet still significant rejection of Cl$^-$ (45%) and K$^+$ (37%). These rejection ratios are comparable to the rejection ratios exhibited by a tight nanofiltration membrane (Filmtec NF90) tested under the same conditions. Note that the DWNT membranes provide an order of magnitude higher flux than the commercial nanofiltration membrane Filmtec NF90.

Modulation of the Electrostatic Field at the CNT Mouth by Solution pH

The size of the CNT membrane pores is 1.3-2.5 times larger than the solvated radii of the ions used in the studies (Table 1). Reported hydrated radii in Table 1 are from reference (Nightingale E R (1959) Phenomenological theory of ion solvation—Effective radii of hydrated ions. *J Phys Chem-US* 63:1381-1387), except for Fe(CN)$_6^{3-}$ (crystallographic radius (Carter D J, Ogden M I, Rohl A L (2003) Incorporation of cyano transition metal complexes in KCl crystals—Experimental and computational studies. *Austr J Chem* 56:675-678)) and Ru(bipy)$_3^{2+}$ (Majumder M, Chopra N, Hinds B J (2005) Effect of tip functionalization on transport through vertically oriented carbon nanotube membranes. *J Am Chem Soc* 127:9062-9070)). Ionic diffusivities are from reference (Newman J, Thomas-Alyea K E (2004) *Electrochemical Systems* (John Wiley & Sons, Inc., Hoboken)), except for Ru(bipy)$_3^{2+}$ (Majumder M et al. as above).

TABLE 1

Studied ionic species: valence z, hydrated radius $\gamma_h$, Stokes radius $\gamma_s$, and bulk diffusivity $D_\infty$.

| Ion | z | $\gamma_h$ [nm] | $\gamma_s$ [nm] | $D_\infty$ [10$^{-5}$ cm$^2$/s] |
|---|---|---|---|---|
| Fe(CN)$_6^{3-}$ | −3 | 0.475 | 0.273 | 0.896 |
| SO$_4^{2-}$ | −2 | 0.379 | 0.230 | 1.065 |
| Cl$^-$ | −1 | 0.332 | 0.121 | 2.032 |
| K$^+$ | 1 | 0.331 | 0.125 | 1.957 |
| Ca$^{2+}$ | 2 | 0.412 | 0.310 | 0.791 |
| Ru(bipy)$_3^{2+}$ | 2 | 0.590 | 0.475 | 0.516 |

For these solute-to-pore size ratios, a sieving effect due to steric hindrance or hydrodynamic interactions with the pore wall may contribute to the observed ion rejection (Dechadilok P, Deen W M (2006) Hindrance factors for diffusion and convection in pores. *Ind Eng Chem Res* 45:6953-6959; and Deen W M (1987) Hindered transport of large molecules in liquid-filled pores. *AIChE* 3:1409-1425). It is also likely that the rejection mechanism involves charge repulsion due to the interaction of the ions with the ionized carboxylic groups at the CNT mouth (Yang D Q, Rochette J F, Sacher E (2005) Controlled chemical functionalization of multiwalled carbon nanotubes by kiloelectronvolt argon ion treatment and air exposure. *Langmuir* 21:8539-8545; and Li P H, Lim X D, Zhu Y W, Yu T, Ong C K, Shen Z X, Wee A T S, Sow C H (2007) Tailoring wettability change on aligned and patterned carbon nanotube films for selective assembly. *J Phys Chem B* 111:1672-1678). To test the importance of the electrostatic interaction, the exclusion characteristics of the CNT membrane at two different solution pH values was measured, one above the pK$^a$ of the COOH group on the surface (pK$_a$=5.5) (Vezenov D V, Noy A, Rozsnyai L F, Lieber C M (1997) Force titrations and ionization state sensitive imaging of functional groups in aqueous solutions by chemical force microscopy. *J Am Chem Soc* 119:2006-2015) (and, also, on a carbon nanotube tip, pK$_a$=4.5 (Wong S S, Joselevich E, Woolley A T, Cheung C L, Lieber C M (1998) Covalently functionalized nanotubes as nanometer-sized probes in chemistry and biology. *Nature* 394:52-55; and Wong S S, Woolley A T, Joselevich H, Cheung C L, Lieber C M (1998) Covalently-functionalized single-walled carbon nanotube probe tips for chemical force microscopy. *J Am Chem Soc* 120:8557-8558)), and one below it.

Figure 2:
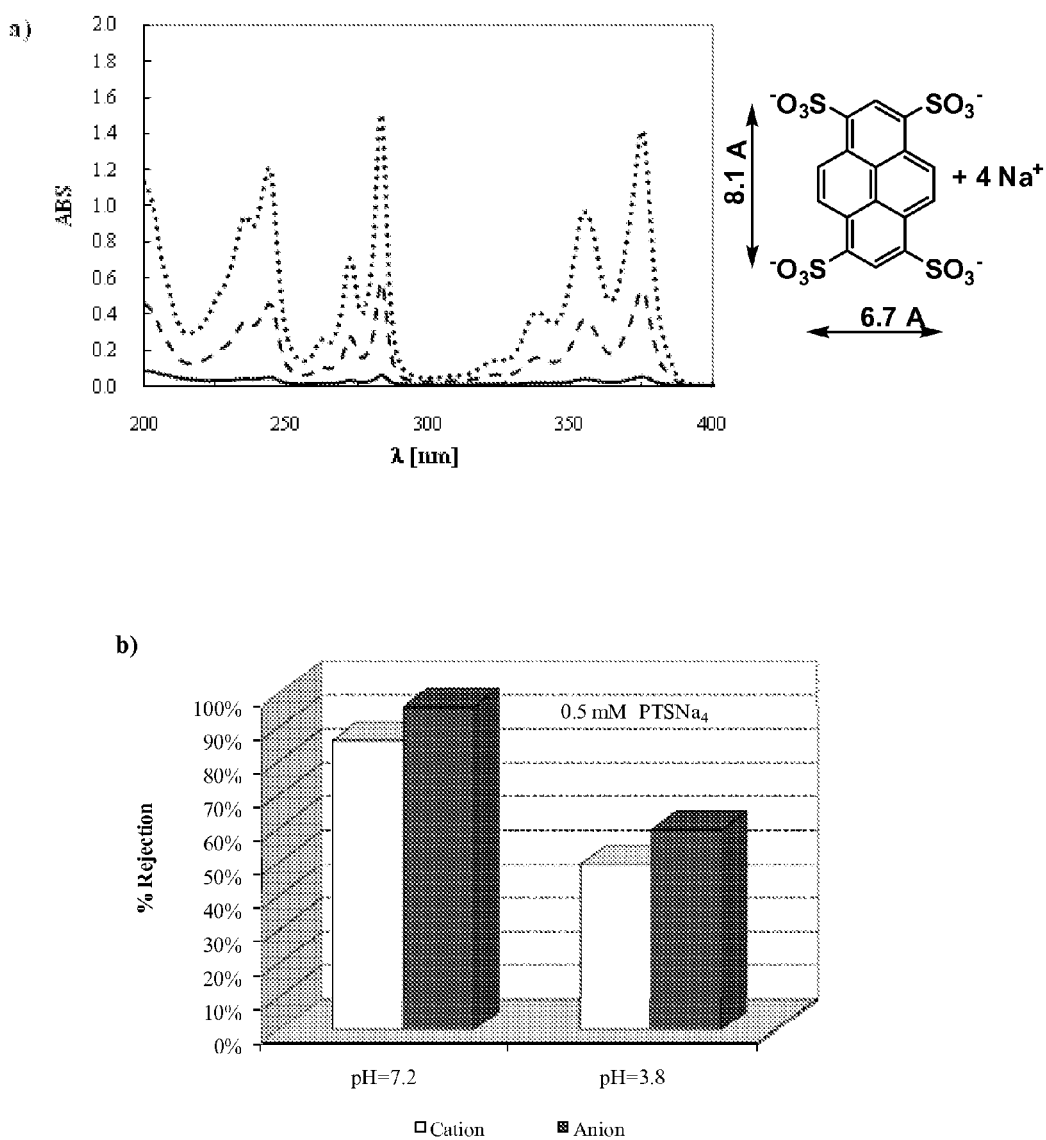
FIG. 2 illustrates an effect of pH on measured rejection for a 0.5 mM $PTSNa_4$ solution: (a) UV spectra for feed (dotted line) and permeate at pH=3.8 (dashed line) and pH=7.2 (solid line); (b) anion and cation rejection at pH=3.8 and pH=7.2.

For these experiments, a 0.5 mM pyrenetetrasulfonic acid tetrasodium salt solution (PTSNa$_4$) is used because the large PTS$^{4-}$ ion remains ionized over a wide range of solution pH values (Nagai Y, Unsworth L D, Koutsopoulos S, Zhang S (2006) Slow release of molecules in self-assembling peptide nanofiber scaffold. *J Control Release* 115:18-25). Also, the selected low solution concentration minimizes possible screening of electrostatic interactions (see next section). As the solution pH changes from a high to a low value, the COO⁻ groups become protonated and neutral, which should result in a sharp drop in the membrane rejection ratio. Indeed, at a pH=7.2, PTS$^{4-}$ absorption in the permeated solution is nearly undetectable (FIG. 2a), indicating an almost complete exclusion (96% of anions, FIG. 2b). However, at pH=3.8, the rejection ratio drops sharply to only 60% (FIG. 2b). These results support a major role of electrostatic interactions in ion rejection.

Ion Rejection and Electrostatic Screening at the CNT Mouth

Figure 3:
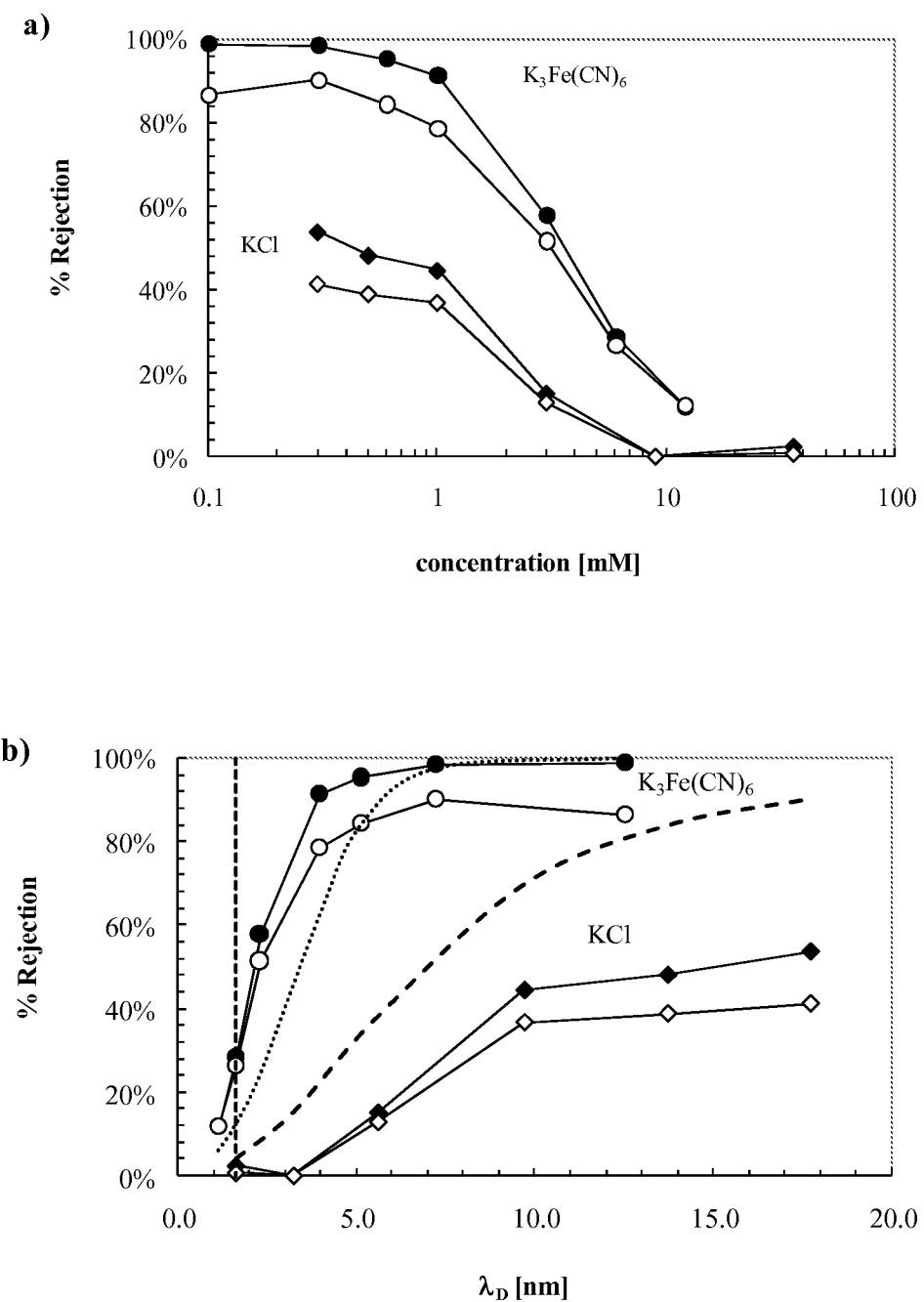
FIG. 3 illustrates a dependence of $K_3Fe(CN)_6$ (circles) and KCl (diamonds) rejections on (a) solution concentration and (b) Debye length. Filled markers correspond to anions, while empty markers correspond to cations. Dashed black vertical line in (b) marks the average CNT diameter. Dotted line and dashed line show the rejection coefficients calculated using Donnan membrane equilibrium theory (Eq. 1) for a 1:3 and a 1:1 electrolyte. To illustrate the trends predicted by the Donnan theory, the membrane charge density is set equal to 3.0 mM.

If electrostatic interactions at the nanotube mouth play a role in ion rejection, then the rejection properties of the membrane should be highly sensitive to the degree of electrostatic screening and, thus, to solution ionic strength. Indeed, we observe that variations in the electrolyte concentration of the solution produce large modulations of the membrane rejection ratio (FIG. 3a-b). For $K_3Fe(CN)_6$ filtration, anion rejection is almost complete and independent of the solution ionic strength as long as the Debye length $\lambda_D$ is larger than the carbon nanotube diameter $d_{CNT}$ (FIG. 3). The Debye length is defined as $$\sqrt{\frac{\varepsilon_o \varepsilon_r k_B T}{2 N_A e^2 I}},$$

where $\varepsilon_o$ and $\varepsilon_r$ are the vacuum and relative permittivity, respectively, $k_B$ is the Boltzmann constant, T the absolute temperature, e the elementary charge, $N_A$ the Avogadro number, and I the ionic strength of the solution. Because our feeds are single salt solutions, I is proportional to the feed concentration, $c_o$, and $\lambda_D \alpha \, C_o^{-1/2}$.

However, when $\lambda_D$ drops down close to $d_{CNT}$, $Fe(CN)_6^{3-}$ exclusion rapidly decays to a value as low as a few percent. $K^+$ rejection shows an identical trend although it is somewhat (~10%) lower than $Fe(CN)_6^{3-}$ rejection at low ionic strength, a difference that disappears with increasing salt concentration. Anion and cation rejections for KCl mirror the trends observed for $K_3Fe(CN)_6$ with the exception that the maximum measured rejection was ~54% for Cl⁻ and 41% for $K^+$. Notably, KCl rejection decays less sharply with decreasing $\lambda_D$. Similar to the trend observed in the $K_3Fe(CN)_6$ rejection experiments, percent anion exclusion is slightly higher than percent cation exclusion (see Supporting Information for a possible explanation of this small difference).

These trends can be rationalized if an exclusion mechanism is considered that accounts for the effect of the Donnan membrane equilibrium. The Donnan model provides a well-known classical description of the electrochemical equilibrium that is established when an ionic solution contacts a charged membrane. Because electrostatic forces with the fixed charges on the membrane counteract the tendency of the co-ions (ions having the same charge sign of the pore charges) to move in the direction of their concentration gradient, charged species distribute unequally between membrane and solution phase. This results in the membrane being enriched with counter-ions and depleted of co-ions. As a consequence, a potential difference is established at the solution/membrane interphase (Donnan potential). When a pressure gradient is applied in a filtration experiment, the Donnan potential tends to exclude co-ions from the membrane. Because of the electroneutrality requirement, which arises from the energetic cost of charge separation, counter-ions have to be rejected as well. Donnan theory provides the following expression for the rejection coefficient, R, of ideal point-charge ions permeating through a charged membrane (Schaep J, Van der Bruggen B, Vandecasteele C, Wilms D (1998) Influence of ion size and charge in nanofiltration. *Sep Purif Technol* 14:155-162):

$$R = 1 - \frac{c_i^m}{c_i} = 1 - \left(\frac{|z_i| c_i}{|z_i| c_i^m + c_x^m}\right)^{|z_i/z_j|}, \quad \text{Eq. 1}$$

where $c_i$ and $c_i^m$, are the concentrations of co-ions in the solution and in the membrane phase respectively, $c_x^m$ is the membrane charge concentration, and subscripts i and j indicate co-ions and counter-ions, respectively. Eq. 1 indeed provides an ion-exclusion dependence on the Debye length that closely approximates the measured trend. The explicit expression of the rejection coefficient dependence on $\lambda_D$ can be easily obtained by substituting $c_i$ with $\alpha/=_D^2$ in Eq. (1), where $\alpha$ is defined as $$\frac{\varepsilon_o \varepsilon_r k_B T}{N_A e^2 (z_i^2 + |z_i z_j|)}.$$

Eq. 1 also predicts that the rejection coefficient decreases faster by decreasing $\lambda_D$ for a 1:3 salt (such as $K_3FeCN_6$) than for a 1:1 salt (such as KCl), which is exactly what the experimental data show (FIG. 3b). The decay of rejection with increasing salt concentration can be explained by the simple reasoning that follows. For a charged pore with diameter greater than the permeating ion, we expect significant exclusion of co-ions when the range of ion electrostatic interaction ($\lambda_D$) with the pore charges is much larger than the pore size, $d_{CNT}$. With increasing salt concentration, as $\lambda_D$ becomes comparable to $d_{CNT}$, a rejection coefficient based on electrostatic interaction quickly decreases because the electrostatic potential decays rapidly with $1/\lambda_D$ away from a charged wall (Newman J, Thomas-Alyea K E (2004) *Electrochemical Systems* (John Wiley & Sons, Inc., Hoboken)). The observed concentration dependence of rejection coefficients alone does not provide a definitive proof that the charges on the CNT entrance are responsible for the reduced ion rejection at larger concentrations since the reduction of ion rejection may simply be a result of the variation of the driving forces for transport rather than a consequence of the reduced range of electrostatic interaction. Indeed, for both neutral and charged solutes at constant applied pressure, an increase in feed concentration reduces water permeation and increases the ion permeation rate. The effective driving force for water permeation is reduced due to the raising osmotic pressure, while the effective driving force for ion permeation is increased due to increased concentration gradient. However, a combination of the concentration dependence and the observed sensitivity of the rejection properties to the change of solution pH does provide a strong indication that electrostatic forces are one of dominant contributors to the ion rejection.

Ion Valence and Ion Exclusion

One of the important consequences of the Dorman exclusion mechanism is the extreme sensitivity of the rejection ratio to the valency of the cationic ($z^+$) and anionic ($z^-$) species present in solution. Indeed, Eq. 1 predicts that the rejection should increase rapidly with the increase of the ratio of $z^-/z^+$. This is a consequence of the fact that, in this theory, the ion rejection exhibited by the membrane is due to the equilibrium partitioning of ions between the solution and membrane phase under the constraints of electroneutrality. Electrostatic forces repel anions from the negatively charged CNT tips while attracting cations. The electroneutrality condition prevents an independent migration of anions and cations. Thus, the overall rejection is determined by a balance between two opposite electrostatic forces: the larger the anion valence relative to the cation valence, the stronger the net repulsive force and, therefore, the salt rejection. On the contrary, a larger cation valence screens more effectively the carboxylic groups on the DWNT entrance, facilitating anion permeation.

To test if ion rejection can be described by the Donnan model, the ion exclusion by the CNT membrane was measured for a series of salts differing in ion valence at the same equivalent solution concentration: $K_3Fe(CN)_6$ (cation-anion valence, $z^+$-$z^-$: 1-3), $K_2SO_4$ (1-2), $CaSO_4$ (2-2), KCl (1-1), $CaCl_2$ (2-1), and $Ru(bipy)_3Cl_2$ (2-1). These measurements were conducted at low ionic strength ($\lambda_D \gg d_{CNT}$) to ensure that the rejection coefficient stays nearly independent of concentration and close to its maximum for a 0.69 bar pressure differential used in our measurements. Remarkably, rejection coefficients measured in these experiments (FIG. 4) show a significant increase for larger $z^-/z^+$ ratios from negligible rejection ($CaCl_2$ and $Ru(bipy)_3.Cl_2$) to nearly complete exclusion ($K_3Fe(CN)_6$). Note also that the rejection of the symmetric salts $CaSO_4$ and KCl ($z^-/z^+$=1) is about the same (~37%), despite the larger charge and size of both the anion and cation of $CaSO_4$ relative to KCl. Similarly, $CaCl_2$ and $Ru(bipy)_3.Cl_2$ ($z^-/z^+$=0.5) permeate almost freely through the DWNT membrane. The measured rejection for $Ru(bipy)_3.Cl_2$ is slightly lower than that of calcium chloride, which is a somewhat striking result considering the much larger size of the $Ru(bipy)_3^{2+}$ cation.

Figure 4:
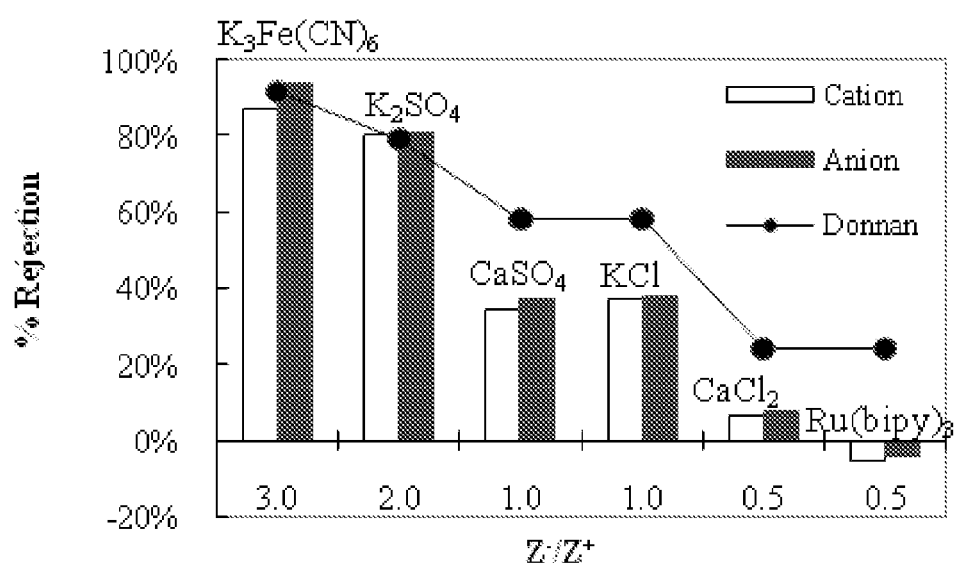
FIG. 4 illustrates rejection coefficients (bars) measured for six salt solutions that have the same equivalent concentration but different ion valence. Points (filled circles) indicate rejections calculated with the Donnan theory, Eq. 1, with a membrane charge density $c_x^m$=2.0 mM (this value was chosen to fit $K_3Fe(CN)_6$ rejection). This density corresponds to about 7 charged groups per nanotube (see Supporting Information in Example 1).

A comparison of the measured ion rejection rates with the prediction of the Donnan model using a reasonable membrane charge density (see Supporting Information below) provides a strong argument for the claim that ion rejection in CNT membranes is dominated by electrostatic interactions (FIG. 4). Moreover, a comparison of the measured rejection ratios with the predictions of the hindered transport model that describes the effects of steric hindrance on the expected ion permeability shows poor correlation (see Supporting Information). Thus, the data strongly suggest that the underlying mechanism of ion exclusion in sub-2-nm CNT membranes is indeed dominated by electrostatic interactions, and that ion size (relative to our DWNT average diameter, 1.6 nm) is much less important.

Molecular dynamics (MD) simulations of uncharged carbon nanotubes (Park J H, Sinnott S B, Alum N R (2006) Ion separation using a Y-junction carbon nanotube. *Nanotechnology* 17:895-900; Peter C, Hummer G (2005) Ion transport through membrane-spanning nanopores studied by molecular dynamics simulations and continuum electrostatics calculations. *Biophys* 89:2222-2234; Leung K, Rempe S B, Lorenz C D (2006) Salt permeation and exclusion in hydroxylated and functionalized silica pores. *Phys Rev Lett* 96:4; and Liu H M, Murad S, Jameson C J (2006) Ion permeation dynamics in carbon nanotubes. *J Chem Phys* 125:084713) also show that pores with diameters>1 nm pose little free-energy barrier for permeation of small ionic species such as $Na^+$ or $K^+$ and that these ions retain their hydration shell almost entirely in pores of these diameters. On the contrary, entrance into subnanometer CNT imposes a high energy penalty because it requires losing part of the hydration shell. MD simulations for other hydrophobic nanopores used as models for biological nanochannels (Beckstein O, Sansom M S P (2004) The influence of geometry, surface character, and flexibility on the permeation of ions and water through biological pores. *Phys Biol* 1:42-52; and Beckstein O, Tai K, Sansom M S P (2004) Not ions alone: Barriers to ion permeation in nanopores and channels. *J Am Chem Soc* 126:14694-14695) reach similar conclusions.

For charged CNTs, theoretical efforts have focused on understanding ion transport through subnanometer CNT and under an external electric field. Both cases of tip localized charges (Joseph S, Mashl R J, Jakobsson E, Alum N R (2003) Electrolytic transport in modified carbon nanotubes. *Nano Letters* 3:1399-1403) and of distributed charges along the pore wall (Park J H, Sinnott S B, Alum N R (2006) Ion separation using a Y-junction carbon nanotube. *Nanotechnology* 17:895-900; Joseph S, Mashl R J, Jakobsson E, Alum N R (2003) Electrolytic transport in modified carbon nanotubes. *Nano Letters* 3:1399-1403; and Sumikama T, Saito S, Ohmine I (2006) Mechanism of ion permeation in a model channel: Free energy surface and dynamics of K+ ion transport in an anion-doped carbon nanotube. *J Phys Chem B* 110:20671-20677) have been considered. Unfortunately, a direct comparison with our experimental data is difficult because none of these studies considered pressure-driven filtration and ion valence effects. Moreover, the diameter of the simulated carbon nanotubes is significantly smaller than our CNT diameters, making confinement effects much more important in the simulated scenario.

Since gap junction (GJ) membrane channels have pore sizes similar to those of the CNTs used in this study (1-2 nm) (Hille B (2001) *Ion Channel of Excitable Membranes* (Sinauer Associates, Inc., Sunderland)), parallels can be drawn between ion rejection mechanisms of these channels and the CNTs used here. Interestingly, small ions are believed to transport through the GJ selectivity filter with little or no loss of their hydration shell. These channels often transport preferentially negatively or positively charged species, and their ion selectivity is also believed to be primarily determined by the presence of charged residues on the GJ pores (Kronengold J, Trexler E B, Bukauskas F F, Bargiello T A, Verselis V K (2003) Single-channel SCAM identifies pore-lining residues in the first extracellular loop and first transmembrane domains of cx46 hemichannels. *J Gen Physiol* 122:389-405; and Trexler E B, Bukauskas F F, Kronengold J, Bargiello T A, Verselis V K (2000) The first extracellular loop domain is a major determinant of charge selectivity in connexin46 channels. *Biophys J* 79:3036-3051). For example, the cation selectivity of Cx46 hemichannels (1.15 nm wide pores) has been demonstrated to be strongly influenced by fixed negative charges located toward the extracellular end of the hemichannel. Replacement of negatively charged residues with positively charged groups imparted anion selectivity to the hemichannel (Kronengold J et al and Trexler E B et al.). Previous studies of GJ pores, together with the data presented in this study, stress the importance of electrostatic interactions in ion rejection mechanisms of pores in the 1-2 nm regime.

Hydrophobic, 1-2 nm wide CNT pores with negatively charged functionalities at their entrance exhibit significant ion rejection when aqueous electrolyte solutions pass through the pore. The observed sensitivity of the rejection to the solution pH and electrostatic screening length suggests that electrostatic interactions dominate over steric effects in governing ion rejection. The observed trends are in agreement with Donnan membrane equilibrium theory. The conclusions are consistent with molecular dynamics studies for ion permeation in uncharged pores, as well as with experimental work on biological ion channels of similar pore sizes, such as gap junctions.

Biological pore channels share a number of structural and functional features with CNTs that make CNT nanofluidic platforms ideal candidates for the realization of a robust, biomimetic system that could exploit the fast transport, selectivity, and gating properties of biological pores. Possible applications range from controlled, nanoscale delivery of therapeutics to molecular sensing. The combination of ultrafast transport and ion exclusion demonstrated in this work could also lead the way towards efficient water desalination. Further reductions in CNT diameter, as well as careful control of the pore surface chemistry, may further improve the membrane performance.

Supporting Information

DWNT membranes with 1.6 nm average pore diameter reproducibly exclude ions. FIG. 5 compare measured rejection coefficients for two different DWNT membranes and with the same salt solutions (0.3 mM $K_3Fe(CN)_6$ in FIG. 5a and 1.0 mM KCl in FIG. 5b), and for the same membrane and salt solution (1.0 mM $K_3Fe(CN)_6$ in FIG. 5c). Inter-membrane variability of measured rejection coefficients is less than 7%, whereas repeated experiments for the same membrane agree within 5%.

Calculation of the Ion Rejection Predicted by the Donnan Model

To calculate the ion exclusion predicted by the Donnan theory, Eq. 1 of the main text is used. In Eq. 1, the molar concentration of the feed after a filtration experiment, $c_i$, is set equal to the initial concentration. Because of the small amount of initial salt solution permeated during an ion rejection measurement, this approximation introduces a negligible error, estimated to be less than 5%. The unknown molar concentrations $c_i^m$ and $c_x^m$ in Eq. 1 have been determined as follows. Eq. 1 is an implicit equation in $c_i^m$ that can be solved once the membrane charge density is known. The membrane charge density $c_x^m$ is assumed to be constant and set equal to 2.0 mM to match, within experimental error, the rejection measured for 0.3 mM $K_3Fe(CN)_6$ solution (see FIG. 4).

A membrane charge density of 2 mM is reasonable. A 2 mM charge density corresponds to ~7 charged groups for each CNT since a CNT of 1.6 nm internal diameter and 3 μm length (typical thickness of our membranes) has an internal volume equal to $6.03 \times 10^{-24}$ $m^3$. The rim of a (14, 14) SWNT having a ~1.6 nm internal diameter contains 29 carbon atoms. Assuming that the charged groups are only at the tips of the CNT, ¼ of the total carbon atoms on the CNT rim are replaced by charged groups in a membrane with a 2 mM charge density.

Hindered Transport Model

The hindered transports model states that in liquid-filled pores of molecular dimensions, a solute experiences hindrance to diffusion and convection due to a combination of particle-wall hydrodynamic interactions and steric restrictions (Deen WM (1987) Hindered transport of large molecules in liquid-filled pores. *AIChE J* 33:1409-1425). For uncharged solutes experiencing no other intermolecular interaction with the pore walls, the hindrance factors for convection, $K_c$, and diffusion, $K_d$, as well as the equilibrium partition coefficient, $\Theta$, are fully defined by the ratio of the solute and pore sizes, $r_s/r_p$. For large membrane Peclet number Pe, diffusion is negligible and the filtrate concentration is determined mainly by the convective fluxes. Pe is defined as $K_c vL/K_d D_\infty$, where v is the convective velocity, L the pore length, and $D_\infty$ is the solute diffusivity in the bulk. Pe is ~10 in our nanofiltration experiments.

Under this condition, at steady state or pseudo-steady state, the predicted rejection coefficient R, defined as $(1-c_i^{permeat}/c_i^{feed})$, is simply given by $$R = 1 - \Theta \cdot K_c \qquad \text{Eq. 2}$$

Expressions for $\Theta \cdot K_c$ as a function of $r_s/r_p$ are found in literature for neutral spheres moving in cylindrical pores (Dechadilok P, Deen W M (2006) Hindrance factors for diffusion and convection in pores. *Ind Eng Chem Res* 45:6953-6959). To calculate the rejection coefficient due only to size effects, we model the ions as uncharged spheres with sizes given by their hydrated radii and we assume that they permeate the DWCN membrane independently. We also consider the case of the neutral salt (anion+cation) modeled as an uncharged sphere with a Stoke's radius obtained from its bulk diffusivity through the Stoke's Einstein relation. Salt diffusion coefficients are calculated from the ionic diffusivities listed in Table 1 as $D_s = (z^+ - z_-)D_+D_-/(z^+D_+ - z^-D_-)$ (Newman J, Thomas-Alyea KE (2004) *Electrochemical Systems* (John Wiley & Sons, Inc., Hoboken)). The hydrated ion radii used here are those in bulk solution and, therefore, only an approximation of the actual size of the ions inside a nanotube. Confinement may affect differently the hydration of different ions. However, simulations (Liu H M, Murad S, Jameson C J (2006) Ion permeation dynamics in carbon nanotubes. *J Chem Phys* 125:084713; Peter C, Hummer G (2005) Ion transport through membrane-spanning nanopores studied by molecular dynamics simulations and continuum electrostatics calculations. *Biophys J* 89:2222-2234; Park J H, Sinnott S B, Alum N R (2006) Ion separation using a Y-junction carbon nanotube. *Nanotechnology* 17:895-900; and Leung K, Rempe S B, Lorenz C D (2006) Salt permeation and exclusion in hydroxylated and functionalized silica pores. *Phys Rev Lett* 96:4) have shown that small ions are able to retain almost entirely their hydration shell in CNT pores with relatively large diameter (>1 nm). Thus, we expect that no large errors are introduced in our calculations by this approximation, and that our conclusions remain valid.

Figure 6:
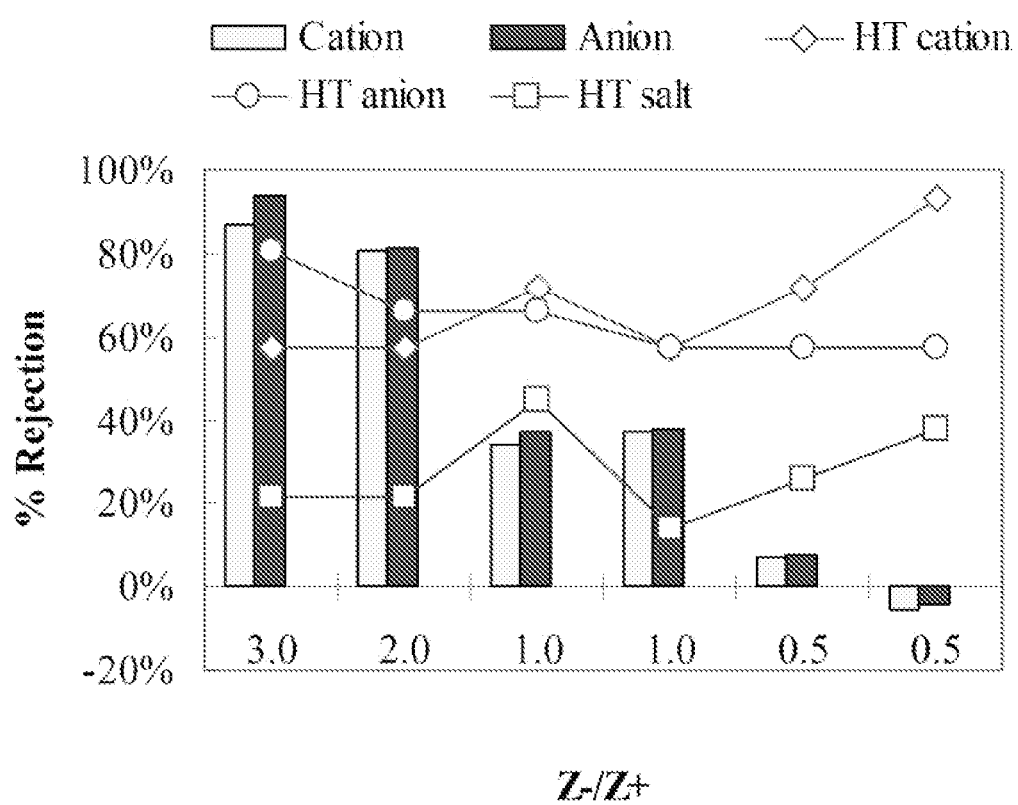
FIG. 6 illustrates rejection coefficient for six salt solutions having the same equivalent concentration but different in valence. Bars represent experimental data for anions and cations: points indicate rejections calculated with the hindered transport (HT) theory, Eq. 2.

FIG. 6 summarizes the predicted and measured rejection coefficients for the six salts considered previously. We attribute the slightly negative rejection measured for $Ru(Bipy)_3.Cl_2$ to a small permeate evaporation before analysis. Measured impact of evaporation on permeate concentration is ~about 4% every 24 h at room temperature. We expect, therefore, that reported rejection coefficients may be a few percent lower than the real one. Clearly, steric constraints and hydrodynamic interactions cannot explain observed trends. In particular, the calculated cation rejection shows opposite behavior with respect to the measured one.

On the Difference Between Anion and Cation Rejection for Single Salt Nanofiltration In many nanofiltration experiments we have measured an anion rejection somewhat larger (≤10%) than the corresponding cation rejection. For several cases, this difference is a few percent larger than the typical experimental error in our measurements. Because overall solution electroneutrality has to be maintained, the excess negative charge associated with the rejected anions has to be balanced by positive charges. A possible source of compensating positive charges is the migration of the highly mobile protons from the permeate to the feed solution. As a consequence, the filtrate pH should have shifted toward basic values relative to the feed. We observe about one unit pH-shift (from pH=6.0-6.5 to pH=7.0-7.5) for the experiments in FIG. 3, which may explain qualitatively the measured small differences in anion and cation rejections. Nanofiltration literature for conventional polymeric and ceramic charged membranes reports several examples of this pH variation (Childress A E, Elimelech M (2000) Relating nanofiltration membrane performance to membrane charge (electrokinetic) characteristics. *Environ Sci Technol* 34:3710-3716; and de Lint W B S, Benes N E (2004) Predictive charge-regulation transport model for nanofiltration from the theory of irreversible processes. *J Membrane Sci* 243:365-377). The effect is expected to be more important at extreme pHs, where protons or hydroxyl ions are more abundant.

Example 2

Figure 7:
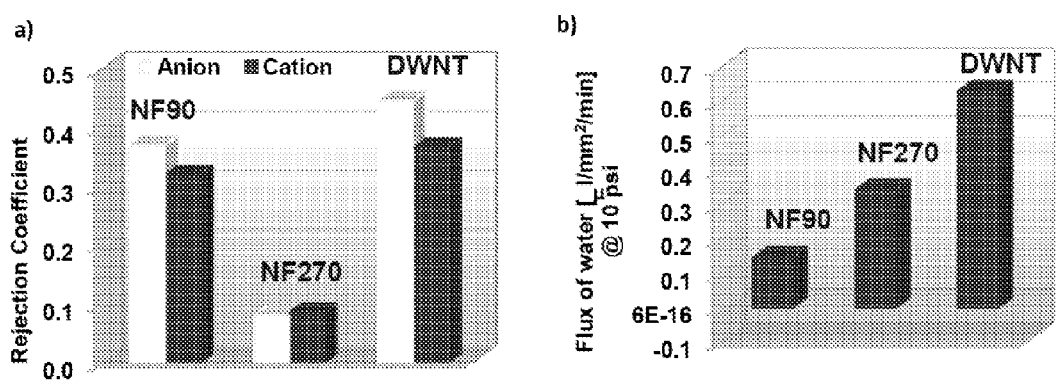
FIG. 7 shows nanofiltration of 1 mM KCl solution at 10 psi. a) rejection coefficient and b) water fluxes measured for DWNT membranes, and commercial nanofiltration membranes NF90 and NF270.

Preliminary experimental data suggest that the DWNT-SiN membranes with CNT tip attached with carboxylic groups outperform typical commercial nanofiltration membranes (without carbon nanotubes) for water softening by providing much larger fluxes at similar monovalent salt rejection or, vice versa, by enabling significantly larger salt rejection at similar water fluxes. For example, a DWNT-SiN membrane rejected 40% of the ion content when a 1 mM KCl solution was filtered at a feed pressure of 10 psi. The corresponding water flux was about 0.63 µl/mm$^2$ min. At the same conditions, Filmtec NF90 and NF270 rejected 35% and less that 10% of the salt, respectively, while allowing water fluxes 5 and 2 times smaller than for the DWNT-SiN membranes. FIG. 7 shows nanofiltration of 1 mM KCl solution at 10 psi. a) rejection coefficient and b) water fluxes measured for DWNT membranes, and commercial nanofiltration membranes NF90 and NF270.

The comparatively high rejection of the DWNT-SiN is unexpected. Ion rejection of nanofiltration membranes is mainly due to a combination of two mechanisms: 1) electrostatic interactions between charged groups in the membranes and electrolytes in solution, and 2) size sieving because of pore dimensions approaching the radius of the hydrated ions. The pore diameter of the commercial nanofiltration membranes is much smaller than the diameters of the DWNT. Reported literature values are about 0.4-0.68 nm (0.54 nm average) for NF90 pore diameters, and 0.57-0.85 nm (0.71 nm average) for NF270, whereas DWNT diameters range between 1-2 nm. Thus, if rejection is based on a sieving mechanism, the commercial nanofiltration membrane should outperform the DWNT-SiN membrane, contrarily to experimental observation. Because rejection of small monovalent ions is tested, the charge-based mechanism may dominate rejection for these membranes. Estimated charge density for the DWNT-SiN is about 1-3 mM. For commercial nanofiltration membranes, charge density may vary significantly with salt type, concentration, solution pH, etc. For 1 mM NaCl solution, the estimated charge density of NF90 is about 20 mM (well within the typical charge densities reported in literature for nanofiltration membranes). Based on these estimates, ion rejection for commercial nanofiltration membranes should be greater than for DWNT-SiN membranes. A possible explanation of the observed better performances of DWNT-SiN membranes is the inherently different localization of the charged groups responsible for the ion rejection. For DWNT-SiN membranes, charged carboxylic groups are concentrated at the pore entrance maximizing their effectiveness. On the opposite, for the polymeric commercial membranes, charged groups are distributed uniformly on the entire membrane volume. Thus, only a fraction of these charges are actively involved in the ion exclusion mechanism.

Example 3

Nanofiltration Experiment for Binary Salt Solutions

Binary KCl/K$_2$SO$_4$ salt solutions with desired composition and constant equivalent concentration were prepared by mixing appropriate amounts of 1 mM KCl and 0.5 mM K$_2$SO$_4$ stock solutions.

The top chamber (feed) of the filtration cell was filled with about 2 ml of binary salt solution, while the bottom chamber (permeate) was sealed with a small vial containing 1 ml of distilled water to limit permeate evaporation before the analysis of ion concentration. The feed solution was pressurized at 0.69 bar with a controlled nitrogen gas line, while the permeate was at atmospheric pressure. After 150-200 µL of solution had permeated through the CNT membrane, samples from both feed and permeate were collected for subsequent analysis by capillary electrophoresis (CE). Rejection coefficients for Cl$^-$ and SO$_4^{2-}$ anions were obtained from the ratio of resolved-peak area of the corresponding ion in the CE chromatogram for permeate and feed samples.

Figure 17:
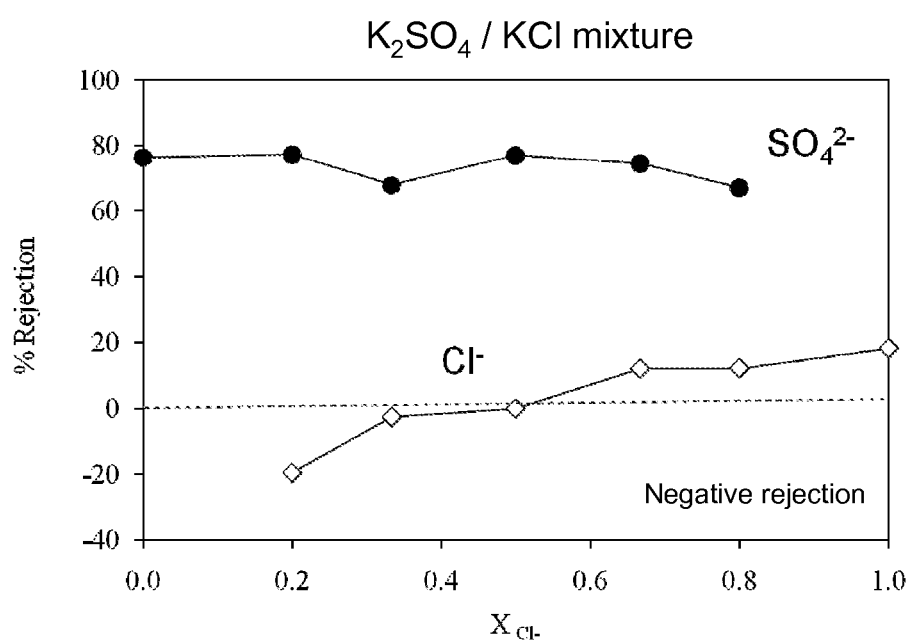
FIG. 17 illustrates an anion rejection for binary $K_2SO_4$/KCl salt solutions as a function of chloride anion mole fraction $X_{Cl^-}$ in the feed solution.

FIG. 17 illustrates the anion rejection for binary K$_2$SO$_4$/KCl salt solutions as a function of chloride anion mole fraction $X_{Cl^-}$ in the feed solution. The chloride mole fraction is defined as the ratio of Cl$^-$ moles and the sum of SO$_4^{2-}$ and Cl$^-$ moles. The equivalent anion concentration of all binary salt solutions is kept constant and equal to 1.0 mM. Filled circles represent experimental rejections for sulfate anions, while empty diamonds are for chloride anions. Sulfate rejection is nearly independent of solution composition, whereas chloride rejection declines with decreasing chloride content in the feed solution.

Experimental results show that sulfate anion rejection is insensitive to feed composition and is in the range 70-80%. On the opposite, the exclusion of chloride anion declines significantly at low chloride mole fractions from about 20% to negative rejections (i.e., the permeate chloride concentration is larger than in the feed). This trend can be explained as follows. At low chloride concentration, a larger proportion of the least rejected anion (here the chloride anion) has to permeate through the membrane to balance the permeation of positively charged potassium ions, as required by the electroneutrality condition. Thus, the lower the feed chloride content the lower the chloride rejection after filtration. The observed negative rejection suggests that monovalent anions (that tend to concentrate in the permeate) can be effectively separated from multivalent anions (that tend to concentrate in the feed) for feeds with a low monovalent anion concentration.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A membrane comprising an array of carbon nanotubes functionalized on at least one end of at least one of the nanotubes with from about 5% to about 100% of the sites available for functionalization are functionalized with members of a first group and optionally the remainder of the sites available for functionalization remain free of functionalization or are functionalized with members of a second group, wherein the nanotubes have average pore size of about 6 nm or less and a matrix material disposed between the nanotubes, and wherein the members of the first group are selected from the group consisting of a polyamide, a polyethylene glycol polymer, a dendrimer or a polyelectrolyte, and the members of the second group are functionalized with a charged group or an uncharged group.

2. The membrane of claim 1, wherein substantially all of the nanotubes of the array are substantially vertically-aligned.

3. The membrane of claim 1, wherein the members of the first are the same or different from each other and the members of the second group functionalizing the membrane are the same or different from each other.

4. The membrane of claim 1, wherein the members of the second group functionalizing the nanotubes are selected from the group consisting of an acidic group, a basic group, or a permanent charged group.

5. The membrane of claim 4, wherein the members of the second group comprise at least one of a carboxylic acid, a sulfonic acid, a phosphonic acid, an amine, and an amide.

6. The membrane of claim 1, wherein the carbon nanotubes are single wall or double-wall nanotubes.

7. The membrane of claim 1, wherein more than 10% of the second group are free of catalyst nanoparticles used for carbon nanotube formation.

8. The membrane of claim 1, wherein the array comprises a tube areal density of at least $4 \times 10^{10}$/square centimeter.

9. The membrane of claim 1, wherein the at least one nanotube has a height of about 0.1 microns to about 500 microns; about 5 microns to about 250 microns; and about 0.1 micron to about 5 microns.

10. The membrane of claim 1, wherein the nanotubes are substantially the same height or of substantially different height.

11. The membrane of claim 1, wherein the matrix material is selected from the group consisting of inorganic material and polymeric material.

12. The membrane of claim 1, wherein the matrix material is selected from the group consisting of ceramic, silicon nitride, polymer, and TEOS oxide.

13. The membrane of claim 1, wherein the matrix material has negligible molecular permeability or is a rigid material.

14. The membrane of claim 1, wherein the matrix material has selective molecular permeability.

15. The membrane of claim 1, wherein the membrane has a thickness of about 0.1 microns to about 2 microns or about 400 nm to about 800 nm.

16. The membrane of claim 1, wherein the matrix material encapsulates the carbon nanotubes or conformally coats the carbon nanotubes.

17. The membrane of claim 1, wherein the matrix material is free of gaps between the outer surface of the nanotubes and the matrix material.

18. The membrane of claim 1, wherein the membrane does not fracture when tested with a one atmosphere pressure drop.

19. The membrane of claim 1, wherein the membrane does not pass 100 nm fluorescently-labeled polystyrene beads or 25 nm fluorescently-labeled polystyrene beads.

20. The membrane of claim 1, wherein the membrane does not pass 2 nm, 5 nm, or 10 nm gold nanoparticles.

21. The membrane of claim 1, wherein the gaps are high aspect ratio gaps of at least about 100 length/diameter or about 1,000 length/diameter or less.

22. The membrane of claim 1, wherein the membrane provides a gas selectivity relative to helium which is higher than that from a Knudsen model.

23. The membrane of claim 1, wherein the at least one nanotube has a height of about 5 microns to about 250 microns.

24. The membrane of claim 1, wherein the at least one nanotube has a height from about 0.1 micron to about 5 microns.

25. A membrane for an enhanced transport of a desalted water from a salted water comprising: a substantially vertically-aligned array of carbon nanotubes, wherein the nanotubes have average pore size of about 1-2 nm and with from about 5% to about 100% of the sites available for functionalization on the nanotubes are functionalized with members of a first group and optionally the remainder of the sites available for functionalization on the nanotubes remain free of functionalization or are functionalized with members of a second group, wherein the members of the first group are selected from the group consisting of a polyamide, a polyethylene glycol polymer, a dendrimer or a polyelectrolyte and the members of the second group are functionalized with a charged group or an uncharged group.

26. A membrane of claim 25, wherein the nanotubes have a charge density of about 1-3 mM.

27. A chip comprising a plurality of membranes of any of claim 1, 25 or 26.

28. A method of separating an analyte from a fluid by passing the fluid containing the analyte through the membranes of any of claim 1, or 26.

29. The method of claim 28, wherein the fluid is sea water, waste water, industrial stream, blood, urine, saliva, or plasma.

* * * * *